(12) United States Patent
Fox

(10) Patent No.: US 6,736,837 B2
(45) Date of Patent: May 18, 2004

(54) METHOD FOR INDUCING HYPOTHERMIA FOR TREATING NEUROLOGICAL DISORDERS

(76) Inventor: James A. Fox, 3708 Carlson Cir., Palo Alto, CA (US) 94306

( * ) Notice: Subject to any disclaimer, the term of this patent is extended or adjusted under 35 U.S.C. 154(b) by 97 days.

(21) Appl. No.: 10/146,378

(22) Filed: May 13, 2002

(65) Prior Publication Data

US 2002/0138121 A1 Sep. 26, 2002

Related U.S. Application Data

(63) Continuation of application No. 10/015,254, filed on Dec. 12, 2001, which is a continuation-in-part of application No. 09/675,810, filed on Sep. 29, 2000, now abandoned, which is a continuation-in-part of application No. 09/523,829, filed on Mar. 13, 2000, now abandoned, which is a continuation-in-part of application No. 08/909,752, filed on Aug. 12, 1997, now Pat. No. 6,090,132.
(60) Provisional application No. 60/256,271, filed on Dec. 15, 2000.

(51) Int. Cl.[7] .................................................. A61F 7/00
(52) U.S. Cl. ........................................ 607/113; 607/96
(58) Field of Search .................................. 607/96–114

(56) References Cited

U.S. PATENT DOCUMENTS

| | | | |
|---|---|---|---|
| 5,190,539 A |   | 3/1993 | Fletcher et al. |
| 5,261,399 A | * | 11/1993 | Klatz et al. |
| 5,417,686 A |   | 5/1995 | Peterson et al. |
| 5,486,208 A | * | 1/1996 | Ginsburg |
| 5,716,386 A | * | 2/1998 | Ward et al. |
| 5,735,817 A | * | 4/1998 | Shantha |
| 5,837,003 A |   | 11/1998 | Ginsburg |
| 5,895,356 A |   | 4/1999 | Andrus et al. |
| 5,913,885 A | * | 6/1999 | Klatz et al. |
| 6,019,783 A |   | 2/2000 | Phillips et al. |
| 6,033,383 A |   | 3/2000 | Ginsburg |
| 6,051,019 A |   | 4/2000 | Dobak, III |

OTHER PUBLICATIONS

Ash et al., "Extracorporeal Whole Body Hyperthermia Treatments for Infection and AIDS," *ASAIO J.* 43:M830–M837 (1997).

(List continued on next page.)

*Primary Examiner*—Robert L. Nasser
(74) *Attorney, Agent, or Firm*—James A. Fox

(57) ABSTRACT

The invention relates generally to methods of treating cancer and other diseases by modulating body temperature. Heat may directed to the hypothalamus of a warm-blooded animal to cool the animal, utilizing the physiological mechanisms that regulate body temperature to effect a compensatory cooling response, thereby lowering body temperature (hypothermia), and rendering other methods of lowering body temperature more effective. Heat may be withdrawn from the hypothalamus of an animal, cooling the hypothalamus, inducing a compensatory increase in body temperature (hyperthermia), and rendering other methods of raising body temperature more effective. Body temperature may be directly modulated by heat-exchange catheter positioned within a blood vessel of a patient. The invention relates generally to methods of treating cancer by inducing hypothermia by directing heat to the hypothalamus, optionally maintaining cancerous tissue at or near to normal body temperature, and optionally applying another cancer treatment. This other cancer treatment may be radiation therapy, chemotherapy, a combination of radiation and chemotherapy, or some other cancer treatment. The invention relates generally to methods of treating diseases including cancer, viral infections, and other diseases, comprising inducing hyperthermia by cooling the hypothalamus, and optionally applying another treatment, for example radiation, chemotherapy, antiviral therapy, or a combination of therapies.

17 Claims, 3 Drawing Sheets

OTHER PUBLICATIONS

Burd et al., "Tumor Cell Apoptosis, Lymphocyte Recruitment and Tumor Vascular Changes Are Induced by Low Temperature, Long Duration (Fever–Like) Whole Body Hyperthermia," *J. Cellular Physiology 177*: 137–147 (1998).

Croghan et al., "A Phase I Study of the Toxicity of regional Hyperthermia With Systemic Warming," *American Journal Clinical Oncol.(CCT) 16*(4):354–358 (1993).

Issels et al., "Ifosfamide Plus Etoposide Combined With Regional Hyperthermia in Patients With Locally Advanced Srcomas a Phase II Study," *Journal Clinical Oncol. 8*(11):1818–1829 (1990).

Keil et al., "Hormonal Secretion Patterns but not Autonomic Effector Responses Elicited by Hypothalamic Heating and Cooling are Altered in Febrile Rabbits," *Journal of Autonomic Nervous System 57*:193–201 (1996).

Maeta et al., "Clincial Evaluation of Total–Body Hyperthermia Combined With Anticancer Chemotherapy for Far–Advanced Miscellaneous Cancer in Japan," *Cancer 59*:1101–1106 (1987).

Marmor, Jane B., "Interactions of Hyperthermia and Chemotherapy in Animals," *Cancer Res. 39*:2269–2276 (1979).

Robins et al., "Whole Body Hyperthermia in the Treatment of Neoplastic Disease," *Radiologic Clinics of North America 27*(3):603–610 (1989).

Shidnia et al. "Clinical Experience With Hyperthermia in Conjunction With Radiation Therapy," *Oncology 50*:353–361 (1993).

Valdagni, R., "International Consensus Meeting on Hyperthermia: Final Report," *Int. Journal Hyperthermia 6*(5):837–877 (1990).

Zablow et al., "Extracorporeal Whole Body Hyperthermia Treatment of HIV Patients, a Feasibility Study," *Int. J. Hyperthermia 13*(6): 577–586 (1997).

* cited by examiner

METHOD FOR INDUCING HYPOTHERMIA FOR TREATING NEUROLOGICAL DISORDERS

CROSS-REFERENCE TO RELATED APPLICATIONS

This application is a continuation of U.S. patent application Ser. No. 10/015,254, filed Dec. 12, 2001, which is a continuation-in-part of patent application Ser. No: 09/523,829 filed Mar. 13, 2000, entitled "Method for Inducing Hypothermia for Treating Cancer," now abandoned which is a continuation-in-part of patent application Ser. No: 08/909,752 filed Aug. 12, 1997, now U.S. Pat. No. 6,090,132, from which applications priority is claimed under 35 U.S.C. §120. U.S. patent application Ser. No. 10/015,254 is also a continuation-in-part of patent application Ser. No. 09/675,810, filed Sep. 29, 2000, entitled "Method and Apparatus for Inducing Hyperthermia" now abandoned from which priority is claimed under 35 U.S.C. §120. U.S. patent application Ser. No. 10/015,254 also claims priority under 35 U.S.C. §119(e) from Provisional Application Serial No. 60/256,271, filed Dec. 15, 2000, entitled "Methods for using heat exchange catheters to induce hypothermia for treating cancer." All the above-named patents and patent applications are incorporated herein by reference in their entirety.

TECHNICAL FIELD

"The invention relates generally to methods and apparatus for inducing hypothermia in an animal, and more particularly relates to methods and apparatus for warming a nasal passage, or a sinus, or the hypothalamus, or a combination of these, of an animal."

BACKGROUND

"More than half-a-million Americans suffer strokes every year, and a similar number suffer head trauma each year. Some of these people die of their injuries; however, most survive with some degree of neurological damage. Although many treatments and therapies have been attempted, none are very effective in reducing neurological damage following stroke, head trauma, or other such condition. One of the most effective therapies known for these and similar conditions is hypothermia, the lowering of body temperature. Even small reductions in body temperature after the initial injury has occurred can reduce damage and improve neurological outcome, if treatment is not delayed too long after the incident. In fact, hypothermia has been a confounding variable in animal experiments directed at discovering pharmacological compounds which may reduce neurological damage following experimentally-induced trauma; some compounds thought to be directly neuroprotective have instead been found to lower body temperature in the small-bodied experimental animals used in studies. When the body temperature of these animals is artificially maintained at the normal level during drug treatment, some of these promising drugs have been found not to be neuroprotective, revealing that the effective treatment was hypothermia, and not the drug. Accordingly, it is desireable to discover a method for inducing hypothermia in humans.

Body temperature is very well regulated in warm-blooded animals. However, the pharmacological compounds that may lower the body temperature of a mongolian gerbil or a rat (with large body surface areas compared to their small volumes) do not effectively produce hypothermia in larger animals such as humans. It is very difficult to cool humans due to our larger mass, smaller surface area in proportion to our volume, and our complex homeostatic mechanisms geared towards maintaining our body temperature.

However, although difficult, it is possible to cool large animals and humans. Hypothermia (the condition of lower-than-normal body temperature in a warm-blooded animal) has been investigated in animals for many years, and has been used on human patients (for example, in heart surgery) for more than forty years. It is known to reduce neurological damage otherwise resulting from cardiac arrest, stroke and trauma. Known methods for inducing hypothermia all involve cooling the outside or inside of an animal, sometimes in conjuction with drugs that disable the animal's homeostatic responses. Present methods for inducing hypothermia include externally applied cold packs, ice blankets, infusion of cold saline into arteries and into the peritoneum of an animal, blowing air across an animal's skin, wetting the skin or hair of an animal, and cooling the air around an animal. One method, preferred by some researchers, includes infusion of saline into the peritoneum of an animal in order to cool a large volume of blood and tissue in contact with the peritoneum. However, this is no simple procedure, but is an invasive procedure that requires puncture of the abdominal wall, infusion of cool or cold saline, and monitoring of fluid and electrolyte balance of the animal for the duration (and beyond) of the procedure. Hypothermia may also be a side-effect of general anesthesia during surgery.

However, these methods are impractical because they require trained personnel and dedicated equipment, and often induce discomfort in the animal or are invasive. In many of the above examples, careful co-ordination and oversight by medical personnel is required since drastic measures need be taken to overcome the normal operation of the animal's physiological responses to cold. These responses include vasoconstriction, shunting of blood away from the limbs and retention of blood in the body core (away from cold blankets, wet skin, etc.) and shivering. Suppression of these responses by muscle relaxants, vasodilators and other drugs may also cause, as side-effects, suppression of other vital body functions associated with breathing, maintenance of blood pressure, heart rate, and other vital bodily functions. These side-effects, such as circulatory shock, may be serious. They increase risk and limit the effectiveness of hypothermia treatments in humans. Thus, there is at present no simple, effective method for inducing and maintaining hypothermia in an animal.

All of the above-mentioned methods for inducing hypothermia, with the possible exception of some potent centrally-active drug regimens that disable thermoregulation, must work to oppose the animal's bodily efforts to maintain body temperature. Difficulties with these techniques arise because the homeostatic mechanisms and physiological responses involved in regulation of body temperature are among the most basic responses in warm-blooded animals. Cooling by cold blankets and dressings is uncomfortable, induces shivering which must be opposed by medication, and causes vasoconstriction which reduces blood flow to the cooled extremities, reducing the effectiveness of the cooling treatment. Cooling by intra-arterial infusion of cold blood or saline is invasive, of limited utility because of limited ability to deliver large volumes of cooled fluid, requires medical equipment and supervision, and may potentially cause vascular, cardiac and neurological (if emboli are created) side-effects. Pharmaceutical treatments that disable thermoregulatory responses often have other effects as well, and require active cooling measures such as those already mentioned in order to lower body temperature of a large animal. Thus, an ideal method for inducing hypothermia in a warm-blooded animal would not require drastic invasive measures or drugs, and would not oppose the animal's physiological temperature control mechanisms, but would make use of them to achieve hypothermia."

Hypothermia—Reduced Temperature

Hypothermia in an animal occurs when the body temperature, or temperature of a body region or organ, becomes reduced below the normal range. Hypothermia has been suggested or shown to be an effective treatment, or useful adjunct to other treatments, for a variety of diseases, including stroke, trauma to the central nervous system, and cancer.

Hypothermia (the condition of lower-than-normal body temperature in a warm-blooded animal) has been investigated in animals for many years, and has been used on human patients (for example, in heart surgery) for more than forty years. For example, U.S. Pat. No. 4,750,493 to Brader is directed to a method for cooling the extracranial area including the face during emergency care of cardiac arrest of severe shock in order to induce vasoconstriction and intracranial hypothermia. This invention is implemented by a topical cold pack described in the patent. U.S. Pat. No. 4,920,963 to Brader is also directed to a method and apparatus for cooling the extracranial area including the face during emergency care of cardiac arrest of severe shock, and discloses an apparatus which includes a watertight shroud for the head. U.S. Pat. No. 5,383,854 to Safar, Strezoski and Klain is directed to a cardio-pulmonary bypass apparatus adaptable to include a module that includes a heat exchanger capable of cooling the blood. U.S. Pat. No. 5,464,834 to Peglion, Goument, Millan and Rivet is directed to chemical compounds acting at a $5\text{-HT}_{1A}$ receptor capable of inducing hypothermia in rats. U.S. Pat. No. 5,474,533 to Ward, Brown and Dzwonczyk is directed to a method and apparatus for treating patients suffering from cardiac arrest, shock, respiratory failure, hypothermia, hyperthermia, and head injury, capable of modulating a patient's body temperature. U.S. Pat. No. 5,486,204 to Clifton is directed to a method for treating severe brain trauma with hypothermia. Hypothermia in human patients was induced by wrapping patients in cooling blankets, and administering drugs such as muscle relaxants and sedatives. All patents, both supra and infra, are hereby incorporated by reference in their entirety.

Hypothermia is Useful in the Treatment of Cancer

Hypothermia can be useful in the treatment of cancer. For example, lowered body temperature has been reported to reduce tumor metastasis in rats (Fisher et al. *Archives of Surgery* 98:347–351 (1969)) and in rabbits (Mandrik, *Bulletin of Experimental Biology and Medicine (USSR)* 47:66–70 (1959)). As long ago as 1940, Smith and Fay (*American Journal of Clinical Pathology* 10:1–12) reported that generalized hypothermia (as low as 74° F., with patients maintained in the low 80s F. for up to 5 to 8 days) in cancer patients led to a reduction in pain and "regressive changes in embryonic cells, particularly in carcinoma" (Id. at page 10).

Hypothermia has been combined with other cancer treatments. Harrison (*Journal of Laryngology and Otology* 81:173–185 (1967)) treated 11 patients with head and neck cancer with chemotherapy during whole-body hypothermia by immersion in an ice bath, and suggested this be the treatment of choice for such patients. Scaly et al. (*British Journal of Radiology* 59(707):1093–1098 (1986)) reported that 10 of 21 mouth cancer patients were free of disease one year after treatment with hyperbaric oxygen and radiation with hypothermia.

Another, related strategy has been to lower the temperature of an animal with a tumor or tumors while locally maintaining the temperature of the cancerous tissue near normal body temperature. Regression and disappearance of tumors in hamsters made hypothermic has been reported where the tumors were artificially maintained at normal body temperature (Popovic and Masironi, *American Journal of Physiology* 211:463–466 (1966); Popovic and Masironi, *Cancer Research* 26:863–864 (1966)). Inducing hypothermia in animals with cancer while maintaining tumor tissue normothermic has enhanced the efficacy of chemotherapeutic agents. Popovic and Masironi (*Cancer Research* 26(1):2353–2356 (1966)) report the regression and disappearance of tumors in hamsters treated with at a 50 mg/kg dose of 5-fluoruracil (5-FU) during hypothermia, with the tumors maintained at normal body temperature, while the same dose of 5-FU did not affect tumor size when given to tumor-bearing animals that were not made hypothermic, or hypothermic animals whose tumors were also hypothermic. Thus, the combination of hypothermia, normothermic tumors, and chemotherapy (the tumors being maintained locally at normal body temperature during application of chemotherapy) has been found to be successful in treating cancer in laboratory animals.

Methods for maintaining cancerous tissue near to or above normal body temperature in a hypothermic animal are the same as those used to locally warm tissues, and have been known for many years. For example, radio-frequency electromagnetic heating for localized tissue heating in cancer therapy was described in 1962 by Shingleton et al. (*Annals of Surgery* 156:408–416). More modern methods include application of ultrasound heating, as for example, may be used to heat the prostate (see, e.g., U.S. Pat. No. 5,895,356 to Andrus et al., Apparatus and method for transurethral focused ultrasound therapy). Other methods include application of warm fluids, application of warm probes, application of radiation, such as infrared, microwave, or ultrasound radiation, inductive heating, and other means.

However, the methods and pharmacological compounds that may lower the body temperature of a laboratory rat or other small animal (with large body surface areas compared to their small volumes) do not effectively produce hypothermia in larger animals such as humans. Cooling humans and other large animals present difficulties due to our larger mass, smaller surface area in proportion to our volume, and our complex homeostatic mechanisms geared towards maintaining our body temperature.

Prior methods for inducing hypothermia include externally applied cold packs, ice blankets, infusion of cold saline into arteries and into the peritoneum of an animal, blowing air across an animal's skin, wetting the skin or hair of an animal, and cooling the air around an animal. Hypothermia may also be a side-effect of general anesthesia during surgery.

Another method of inducing hypothermia comprises cooling by intra-arterial infusion of cold blood or saline. An example of such a method may be found in, e.g., U.S. Pat. No. 5,383,854 to Safar et al. A variant of the method of cooling the blood comprises insertion of a heat-exchange catheter into a body lumen of an animal effective to cool surrounding body fluids and tissues. Heat exchange catheters for inducing hypothermia are disclosed in Ginsburg, U.S. Pat. No. 5,837,003; Ginsburg, U.S. Pat. No. 5,486,208; Ginsburg, U.S. Pat. No. 6,033,383; Philips et al., U.S. Pat. No. 6,019,783; and Dobak, U.S. Pat. No. 6,0510,19.

However, these methods often induce discomfort in the animal or are invasive. In addition, drastic measures often need be taken to overcome the animal's normal physiological responses to cold. These responses include vasoconstriction, shunting of blood away from the limbs and retention of blood in the body core (away from cold blankets, wet skin, etc.) and shivering. Suppression of these responses by muscle relaxants, vasodilators and other drugs may also cause, as side-effects, suppression of other vital body functions associated with breathing, maintenance of blood pressure, heart rate, and other vital bodily functions. These side-effects, such as circulatory shock, may be serious. They increase risk and limit the effectiveness of hypothermia treatments in humans. Thus, these prior methods when used alone do not provide a simple, effective method for inducing and maintaining hypothermia in an animal.

An ideal method for inducing hypothermia in a warm-blooded animal would not oppose the animal's physiological temperature control mechanisms, but would make use of them to achieve hypothermia. Accordingly, improved methods of inducing hypothermia in larger animals, including human patients, are desired.

Hyperthermia—Elevated Temperature

Hyperthermia in an animal occurs when the body temperature, or temperature of a body region or organ, becomes elevated above the normal range. Mild hyperthermia is a normal response to many forms of infection, as exemplified by fever. Hyperthermia has been suggested or shown to be an effective treatment, or useful adjunct to other treatments, for a variety of diseases.

Hyperthermia has been used to treat cancer. Observations of tumor regression in patients who had suffered from fevers were noted over a hundred years ago (Coley W B: Ann Surg 14:199 (1891)), and deliberate hyperthermia was reported as a treatment for tumors of the extremities nearly forty years ago (see, e.g., Stehlin, J S et al. Amer J Surg 105:60 (1963)). Whole body hyperthermia has been applied as a cancer treatment for a quarter of a century (see, e.g., Parks et al. in: F K Storm, ed. Hyperthermia in Cancer Therapy, G K Hall, Boston, Mass. 1995, pp. 407–446; Frazier H O, Proceed Am Acad Cardiovasc Perf 3:99 (1982); Herman et al., Cancer Treat Rep 66:259 (1982); Maeta et al. Cancer 59:1101 (1987)). Such work continues to the present day. For example, tumor cell apoptosis was reported in tumor-bearing mice exposed to hyperthermia for 6 to 8 hours (Burd et al., J. Cell. Physiol. 177:137 (1998)). Whole body hyperthermia has been found to relieve pain and to control tumor growth in a significant number of patients. A review on hyperthermia may be found in the International Consensus Meeting on Hyperthermia: Final Report, Valdagni et al., Int. J. Hyper. 7(5):837(1990).

Cancer cells are more sensitive to elevated temperature than normal cells (see, e.g., Chen et al. Int. J. Cancer 4:166 (1969), Giovanella et al. Cancer Res. 36:3944 (1976) and Robins et al., Radiol. Clin. North Am. 27:603 (1989)). Hyperthermia has been shown to enhance the cytotoxicity of drugs (Hahn et al., Cancer Res. 37:761 (1977); Marmor, Cancer Res. 39:2269 (1979)) and clinical studies have shown that the amount of hyperthermia is significantly related to clinical response in cancer patients receiving regional hyperthermia with their chemotherapy (see, e.g., Issels, et al., J. Clin. Oncol. 8:1818 (1990)). Similarly, hyperthermia has also been shown to enhance the cytotoxic effects of radiation treatments (see, e.g., Shidnia et al., Oncology 50:353 (1993), and of combined radiation and chemotherapy treatments.

In addition, novel cancer therapies may be enhanced by hyperthermia. For example, gene therapy utilizing heterologous gene expression linked to a heat shock protein promoter was enhanced by systemic hyperthermia in tissue culture, and hyperthermia enhanced the effects of adenovirus vectors containing heat-inducible interleukin expression on tumors in mice (Huang et al., Cancer res. 60:3435 (2000)).

Other diseases may be caused by infectious agents such as viruses, bacteria, fungi, parasitic or other organisms. A common reaction to many infections is fever, which may be directly helpful in overcoming the infection or may act to enhance the immune response and so aid in ridding the body of the infectious agents. Hyperthermia thus may be used to treat, or to enhance treatments, of infectious diseases. For example, hyperthermia has been used to treat HIV infections in humans (Ash et al., ASAIO J. 43:M830 (1997); Zablow et al., Int. J. Hyperthermia 13:577 (1997)).

Methods for raising body temperature, and so warming the whole body, include immersion in hot baths or situation of the subject in a hot chamber, use of microwave radiation, and chemical means, such as by administration of pyrogens. Some methods for local warming of tissue have been known for many years. For example, radio-frequency electromagnetic heating for localized tissue heating in cancer therapy was described in 1962 by Shingleton et al. (*Annals of Surgery* 156:408–416). More modern methods include application of ultrasound heating, as for example, may be used to heat the prostate (see, e.g., U.S. Pat. No. 5,895,356 to Andrus et al., Apparatus and method for transurethral focused ultrasound therapy). Other methods include application of warm fluids, application of warm probes, application of radiation, such as infrared, microwave, or ultrasound radiation, inductive heating, and other means. Examples of apparati that may be used to locally warm tissue or body fluids, or to locally cool tissue or body fluids, are disclosed in, for example, U.S. Pat. Nos. 5,486,208, 5,837,003, and 6,033,383 to Ginsburg; U.S. Pat. No. 6,019,783 to Phillips et al.; U.S. Pat. No. 6,051,019 to Dobak; U.S. Pat. No. 5,190,539 to Fletcher et al. and U.S. Pat. No. 5,417,686 to Peterson et al.). Regional heating may be more readily achieved or may be enhanced when combined with whole body hyperthermia (Croghan et al., Am. J. Clin. Oncol. 16:354 (1993)).

All of the above-mentioned methods for inducing hyperthermia, with the possible exception of some potent centrally-active drug regimens such as use of pyrogens, must work to oppose the animal's bodily efforts to maintain body temperature. However, the homeostatic mechanisms and physiological responses involved in regulation of body temperature are among the most basic responses in warm-blooded animals. For this reason, these techniques suffer from the disadvantage that the animal's normal physiological responses are actively opposing the efforts to induce hyperthermia. Thus, an ideal method for inducing hyperthermia in a warm-blooded animal would not oppose the animal's physiological temperature control mechanisms, but would make use of them to achieve hyperthermia. Accordingly, improved methods of inducing hyperthermia in larger animals, including human patients, are desired.

SUMMARY OF THE INVENTION

"Known methods for inducing hypothermia all involve cooling the outside or inside of an animal, sometimes in conjunction with drugs that disable the animal's homeostatic responses. It is new and unsuggested in the art to apply heat in an effort to reduce body temperature. The present invention is directed to a method and apparatus for applying heat to the hypothalamus of a warm-blooded animal in order to utilize the physiological mechanisms that regulate body temperature to effect a compensatory cooling response, thereby lowering body temperature. The present invention takes advantage of physiological temperature-regulatory mechanisms and makes direct use of their action, instead of striving to oppose or disable them.

It is well-known that the main brain center for regulation of body temperature is in the hypothalamus, a brain structure situated in humans just above the pituitaty gland. Decreasing the temperature of the hypothalamus, as occurs when core body temperature is reduced, triggers compensatoxy responses to cold, such as vasoconstriction and shivering. Conversely, warming the hypothalamus triggers compensatory responses that cool the animal, such as vasodilation and sweating. Thermoregulatory responses can be quite effective, as humans routinely live and work in environments where the external temperature is higher or much lower than normal body temperature.

The hypothalamus is very sensitive to small changes in body temperature. A temperature change of 0.2 degrees Celsius (.degree. C.) is sufficient to trigger sweating in a human subject. Sweating is a major mechanism for cooling in humans. Sweating will continue as long as the hypothalamic temperature is above its setpoint for temperature control. Thus, for example, if the temperature of the hypothalamus in a human patient is raised to about 0.2.. degree. C. or more above its setpoint, the patient will respond with such physiological cooling responses as vasodilation and sweating. These responses may continue indefinitely in response to sustained raised temperature of the hypothalamus. These physiological cooling responses will act to lower the body temperature of the patient.

In humans, the hypothalamus is located near to the sphenoid sinus, one of the sinuses accessible through the nose or mouth. Heat may be applied via the sinuses, or more particularly to the sphenoid sinus, in order to warm the hypothalamus and so to trigger a cooling response. Alternatively, heat may be applied directly to the hypothalamus. Heating of the hypothalamus may be accomplished with little heating of surrounding brain regions. Heat applied near the surface of the skull will penetrate a small distance, but blood flow and other thermal effects will cause the heating to be localized to the portion of the brain nearest the application of the heat. Thus, mild local heating of the sphenoid sinus or other nasal passages or sinuses in order to warm the bypothalamus would not cause undue heating of other portions of the brain. Alternatively, warming the nasal passages themselves can trigger sweating and so be effective for lowering body temperature.

Accordingly, a primary object of the present invention is to provide a method for inducing hypothermia which does not require cooling measures such as application of cold packs, cold blankets, infusion of cold saline, does not require drastic invasive measures or drugs, and would not oppose an animal's physiological temperature control mechanisms, but would instead make use of them to achieve hypothermia.

It is a further object of the invention to provide a method of inducing hypothermia by applying heat to a nasal passage.

It is a further object of the invention to provide a method of inducing hypothermia by applying heat to a sinus of an animal. In particular, it is an object of the present invention to provide a method of inducing hypothermia in a person by applying heat to a sphenoid sinus.

It is a further object of the invention to provide a method of inducing hypothermia by warming the hypothalamus of an animal.

It is another object of the invention to provide an apparatus for warming a nasal passage of an animal.

It is another object of the invention to provide an apparatus for warming a sinus of an animal.

It is a further object of the invention to provide an apparatus for warming a sphenoid sinus.

It is another object of the invention to provide an apparatus for warming the hypothalamus of an animal.

It is another object of the invention to provide an apparatus for introducing compounds into a nasal passage of an animal.

It is a further object of the invention to introduce compounds into a sinus of an animal.

Additional objects, advantages and novel features of the invention will be set forth in part in the description which follows, and in part will become apparent to those skilled in the art upon examination of the following, or may be learned by practice of the invention.

In one aspect, the invention is a method for inducing hypothermia which comprises providing a heat-generating means and, with this heat generating means, applying heat to a nasal passage, or a nasal passage and a sinus, or a nasal passage, sinus and hypothalamus, or to a sinus and hypothalamus, or to the hypothalamus. This application of heat to a nasal passage, or a nasal passage and sinus, or sinus and hypothalamus, or hypothalamus will result in a physiological response effective to lower the body temperature of the animal so treated.

In another aspect, this invention is an apparatus for applying heat to a nasal passage, or a nasal passage and a sinus, or a nasal passage, sinus and hypothalamus, or to a sinus and hypothalamus, or to the hypothalamus. Application of heat through the use of said apparatus to a nasal passage, or a nasal passage and a sinus, or a sinus and the hypothalamus, or the hypothalamus will result in a physiological response effective to lower the body temperature of the animal so treated."

Figure 1:
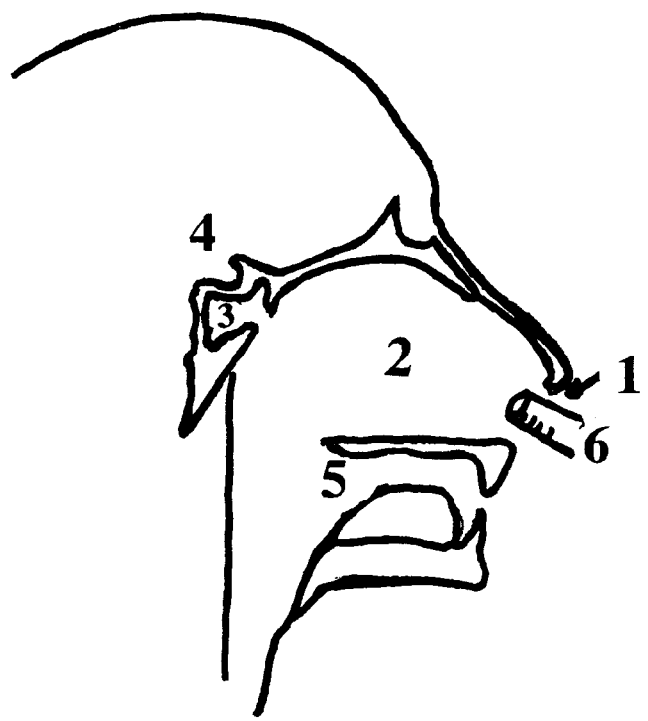
FIG. 1 is a cross-sectional view of a human head, showing placement of a tube in a nostril.
Figure 2:
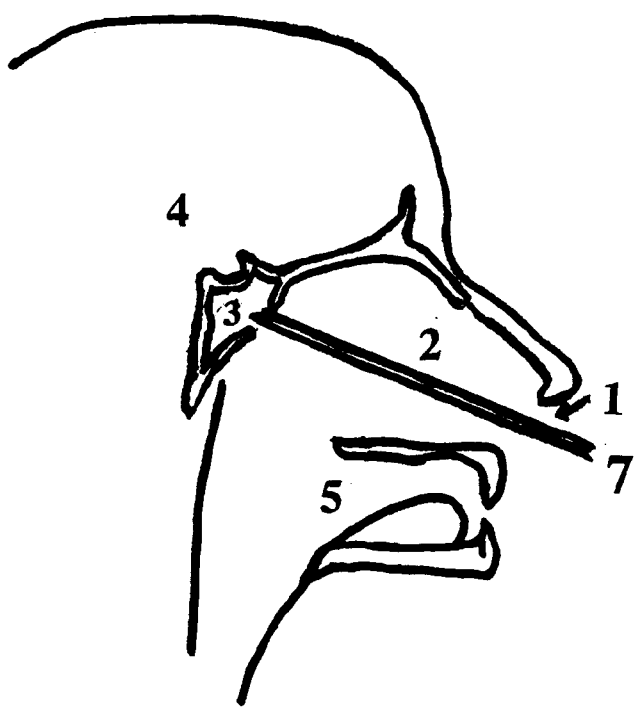
FIG. 2 is a cross-sectional view of a human head, showing placement of a temperature-modulating device into the sphenoid sinus.
Figure 3:
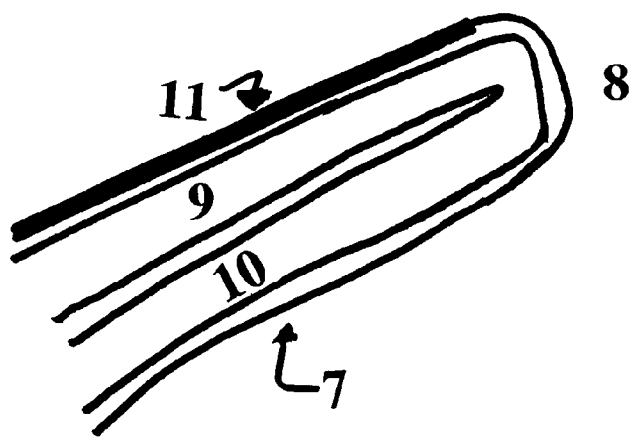
FIG. 3 is a cross-sectional view of a dual-lumen catheter with an occluded end.
Figure 4:
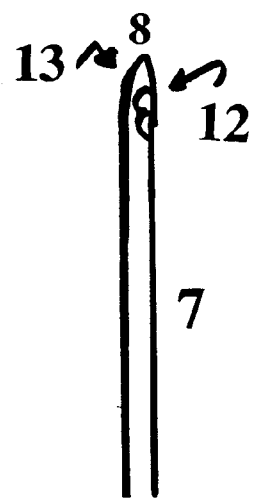
FIG. 4 is a cross-sectional view of an electrical temperature-modulating device with a thermal sensor.

"It is known that hypothermia is one of the most effective therapies available for stroke victims, head trauma victims, and others suffering similar diseases and injuries. Known methods and devices for inducing hypothermia in an animal rely on cooling methods, cooling devices or drug therapies that impair normal body temperature regulation. It is novel to propose warming to induce hypothermia. It is also known that body temperature is well-controlled in warm-blooded animals. The brain regions most important in the regulation of body temperature are in and near the hypothalamus.

It is known that small changes in hypothalamic temperature will cause physiological responses that act to restore body temperature to normal. It is novel to suggest, as is suggested in the present invention, that inducing small changes in hypothalamic temperature can be used for therapeutic effect. In addition, infusion of compounds such as melatonin also affect body temperature.

It is known that the hypothalamus 4 in humans is located near to the sphenoid sinus 3, a sinus which is accessible from the outside of a person via nasal passages 2 and the nostrils 1 and via the oral passage 5. A novel aspect of the present invention is the recognition that application of heat to the sphenoid sinus will warm the hypothalamus and cause a physiological cooling response. Warming of the sphenoid sinus will warm the hypothalamus of a person with normal blood flow but will not greatly warm other brain regions. Modeling suggests that the temperature near to a heat source in a well-perfused brain rises significantly only at the points nearest the heat source. Thus, application of heat to a nasal passage, sinus or directly to the hypothalamus will have only local direct effects on brain temperature, will not significantly raise temperature in other, more distal, brain regions, and will lead to global hypothermia.

The exact parameters of warming a nasal passage, sinus or hypothalamus, or combinations of these, may vary, as will be appreciated by those skilled in the art of medical practice, but will necessarily involve providing a warming means, applying said warming means so as to warm the hypothalamus or sinus or nasal passages, or combinations of these, to between about 38° C. and about 50° C. As said warming means is being applied, compounds may be introduced into a nasal passage or sinus. In some cases, it may be desirable as well to apply cooling measures to the animal, such as blowing air across exposed skin, applying cold dressings to exposed skin, and so forth. However, moderate cooling measures, if any, are preferred, since lowering the skin temperature will raise the hypothalamic temperature setpoint. For this reason, it may be advantageous to warm portions of the skin in order to lower the hypothalamic setpoint and so aid in maintaining a lowered body temperature.

DESCRIPTION OF APPARATUS OF THE INVENTION

Heat may be applied to a nasal passage or a sinus or to a nasal passage and a sinus through the breathing of a warm gas, such as air mixed with steam or water mist (in a ratio of approximately 0% to 40% by volume) at a temperature between about 38° C. and about 50° C., although other temperatures may also be effective. Preferred temperatures are between about 38° C. and 43° C. This gas may be supplied, for example, to a nasal passage via a hollow tube 6, of a size smaller than a human nostril. Tubes effective for this purpose are approximately 0.1" to approximately 0.5" in outer diameter, may be thin-walled or thick-walled, and may be made, for example, of Tygon tubing. This tube may be inserted a short distance (for example, less than 0.5") into a nasal passage, or may be inserted farther into a nasal passage (for example, approximately 1" or more). Care must be taken that the animal breathes sufficient oxygen for health, and that sensitive nasal tissue is not scalded. If higher temperature gases are used, or higher fractions of steam or other warm gas, then smaller diameter tubes which do not fully occlude the nostril and so allow passage of air into the nasal passage are preferred. If lower temperature gases, nearer to 38° C. than 50° C., are used, then larger diameter tubing which occludes the nostril may be used.

Similarly, heat may be applied to a sinus, preferably the sphenoid sinus, through direction of a heated gas such as air mixed with steam via a tube or catheter 7. This heated gas may be air mixed with steam (in a ratio of approximately 0% to 40% by volume) at a temperature between about 38° C. and about 50° C., although other temperatures may also be effective. Preferred temperatures are between about 38° C. and 43° C. This gas may be supplied, for example, to a sinus by a hollow tube with an outside diameter of between about 0.05" and about 0.25". This hollow tube may be thin-walled or thick-walled, and is made, for example, of about 10 cm of flexible tubing with a smooth 4 mm curve at the distal end. This tube may be inserted through a nostril or through the mouth and oral cavity to gain access to a nasal passage above the palate and then into a sinus. Insertion of this tube may be aided by a guide tube, a guide wire, or other implement. Care must be taken that sensitive tissue is not scalded or damaged during insertion. Insertion of this tube is preferably done using methods in common use for introduction of drain tubes into inflamed sinuses for the purpose of draining accumulated fluids.

A nasal passage or sinus may be also warmed by an apparatus which is itself heated and delivers heat. One such apparatus comprises a closed-ended flexible tube containing warm gases, such as the mixtures of steam and air, or other warm gases, or preferably containing a warm fluid, such as warm saline or other liquid, capable of being introduced into a nasal passage or sinus. Warm fluids are preferred over warm gases in this embodiment because their higher heat capacity and greater mass make them more effective to warm the tissue with which they are in contact. The temperature of said gas or fluid may be between about 38° F. and 50° C. Preferred temperatures are between about 38° C. and 43° C. Such an apparatus can be a tube with a single lumen and a distal end blocked to prevent outflow of hot gases or fluids. In a preferred embodiment, this apparatus comprises a tube with at least two inner lumens, at least one for inflow of warm fluid or gas 9, at least one for outflow of warm fluid or gas 10, with a distal end of said tube blocked to prevent outflow of the warm fluid or gas enclosed 8. Constant flow of said warm fluid or gas is maintained to provide continuous heating to the nasal passage or sinus. In a preferred embodiment, said closed end is a distal end comprised of thinner wall thickness than the lateral wall of the apparatus. An effective thickness for the blocked distal end is between about about 0.001" and about 0.05". In another preferred embodiment, said distal end is constructed of a thin flexible material, such as latex rubber or polyethylene of a thickness between about 0.001" and about 0.05" effective for transferring heat and capable of expanding or "ballooning out" to fill space surrounding it under application of internal positive pressure. This apparatus may be inserted through a nostril or through the mouth and oral cavity and then to a nasal passage above the palate and into a sinus. Insertion of this apparatus may be aided by a guide tube, a guide wire 11, or other implement. Care must be taken that sensitive tissue is not scalded or damaged during insertion. Insertion of this apparatus is preferably done using methods in common use for introduction of drain tubes into inflamed sinuses for the purpose of draining accumulated fluids.

Another such apparatus effective to warm a nasal passage or sinus comprises an electrical warming device 12 attached at an end of a flexible tube, rod or catheter capable of being introduced into a nasal passage or sinus. Said electrical warming device may be a thermocouple, Peltier device, electrical heating element, or the like. In a preferred embodiment the electrical warming is obtained by passing electrical current through an insulated coil of nichrome wire (30 to 36 AWG, coil outer diameter 0.04") connected to insulated copper or silver wires (26 to 30 gauge, twisted wire) insulated with a flexible insulating coating of an insulating material such as polyimide or epoxy. The heating element is preferably shaped in a helical coil with an outer dimension of about 0.08" diameter and contained inside an insulating coating. Effective temperatures at the heating element are between about 38° C. and about 50° C. Preferred temperatures are between about 38° C. and about 43° C. to provide warming of the nasal passage or sinus. In a preferred embodiment, a temperature sensor 13 is enclosed with the coil to provide temperature feedback to control the applied temperature. This apparatus may be inserted through a nostril or through the mouth and oral cavity and to a nasal passage above the palate and then into a sinus. Insertion of this apparatus may be aided by a guide tube, a guide wire, or other implement. Care must be taken that sensitive tissue is not scalded or damaged during insertion. Insertion of this apparatus is preferably done using methods in common use for introduction of drain tubes into inflamed sinuses for the purpose of draining accumulated fluids.

Heating of the hypothalamus directly may be accomplished by insertion of heated tubes or electrical devices, and other devices of similar effects, directly into the hypothalamus though surgical procedures. Preferred apparatus are not flexible tubes, but are made of medical grade stainless steel 14, of an outside diameter between about 0.01" and about 0.08". Electrical methods of heating are preferred over methods utilizing heated fluids or gases for this embodiment of the invention. Preferred electrical methods and apparatus include heating elements such as thermocouples, Peltier devices and resistive heating wires such as Nichrome wire provided at the tips of stainless steel rods. In addition, the delivery of radio-frequency current is effective to warm the hypothalamus. Electrical stimulation of neurons in the hypothalamus is also effective to stimulate hypothalamic neurons to trigger a physiological cooling response.

Heating of the hypothalamus may be effected by infrared radiation delivered to the inside of the sphenoid sinus or nasal passage by an infrared source such as a heated coil inside a thermally cooled jacket. In this embodiment, warming of the hypothalamus is effected by either infrared radiation alone, or by infrared radiation along with heat delivered to the hypothalamus by conduction through intervening tissue.

Physiological cooling responses may be initiated by introduction of chemical compounds into a nasal passage and a sinus, at the same time as warm gases or heat is introduced, or in the absence of said heating. Compounds such as melatonin, capsaicin and other compounds are effective to induce a physiological cooling response. Effective concentrations of melatonin are between about 0.1 nM and about 100 nM. Effective concentrations of capsaicin are between about 1 nM and about 1 uM."

DETAILED DESCRIPTION OF THE INVENTION

The hypothalamus is very sensitive to small changes in body temperature. For example, if the temperature of the hypothalamus in a human patient is raised above its setpoint, the patient will respond with such physiological cooling responses as vasodilation and sweating. The physiological cooling responses may continue indefinitely in response to sustained raised temperature of the hypothalamus. These physiological cooling responses will act to lower the body temperature of the patient. Similarly, if the temperature of the hypothalamus in a human patient is lowered below its setpoint, the patient will respond with physiological warming responses. The physiological warming responses may continue indefinitely in response to sustained reduced temperature of the hypothalamus.

In humans, the hypothalamus is located near to the sphenoid sinus, one of the sinuses accessible through the nose and mouth. Heating, or directing heat to, the hypothalamus may be applied indirectly, for example, via the sinuses, or more particularly to the sphenoid sinus, in order to warm the hypothalamus. Heating applied via the sinuses effective to raise the temperature of the hypothalamus above its setpoint will trigger a cooling response, thereby lowering body temperature. In addition, other body cooling means may be applied to the animal before, during and after the period of hypothalamic warming. Such other cooling means may include, but are not limited to, cold pads, cold or wet blankets, cold baths, cold fluids, cold gases, cooling of the blood, ingestion or infusion of cold fluids, and other means.

Alternatively, the hypothalamus may be directly or indirectly cooled to induce a warming response. Cooling, that is withdrawal of heat energy, may be applied indirectly, for example, via the sinuses, or more particularly to the sphenoid sinus, in order to cool the hypothalamus. Cooling applied via the sinuses effective to lower the temperature of the hypothalamus below its setpoint will trigger a warming response, thereby raising body temperature.

Cooling of the hypothalamus may be accomplished with little cooling of surrounding brain regions. Cold applied near the surface of the skull will penetrate a small distance, but blood flow and other thermal effects will cause the resultant cooling to be localized to the portion of the brain nearest the application of the cold. Thus, mild local cooling of the sphenoid sinus or other nasal passages or sinuses in order to cool the hypothalamus would not cause undue cooling of other portions of the brain. Alternatively, cooling the nasal passages themselves can be effective for raising body temperature. In addition, other warming means may be applied to the animal before, during and after the period of hypothalamic cooling. Such other warming means may include, but are not limited to, warm pads, warm blankets, heating lamps, hot baths, hot fluids, hot gases, electromagnetic heating including microwave heating, ultrasonic heating, warming of the blood, ingestion or infusion of warm fluids, breathing warm gases, and other means.

Definitions

Before the present methods and apparatus are disclosed and described, it is to be understood that this invention is not intended to be limited to the specific methods, means and apparatus disclosed herein. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly states otherwise. Thus, for example, reference to "a sinus" includes more than one sinus.

The term "animal" is meant to include humans and other warm-blooded animals.

The term "body temperature" is used in its conventional sense to mean the internal temperature of an animal, as may be measured orally, rectally, or other way.

The term "normal body temperature" refers to temperature of about 37° C., that is, preferably between about 35° C. to about 40° C. most preferably between about 36° C. to about 38° C.

The term "cancerous tissue" refers to cells, or groups or aggregates of cells, that are cancerous.

The term "cancerous condition" refers to the condition of an animal with cancerous tissue, such as cancerous cells or a tumor, or other cancer.

"Cancer treatment" is any therapeutic or palliative treatment directed at cancerous tissue, cancerous cells, or the symptoms of cancer.

The term "cool" is used in its conventional sense to mean the reduction in thermal energy content or warmth; the verb-form of the term, "to cool," is used herein to mean to transfer thermal energy from, to reduce the temperature of, the object or location being cooled.

The term "cold" is used in its conventional sense to mean having a lower temperature than the surroundings. "Application of cold" means to position a cold object, gas or fluid so as to remove heat from the material near to the object or fluid. Similarly, "application of cold temperatures" means to apply, to a body tissue, an object, gas or fluid with a temperature lower than that of the body tissue.

The term "fluid" is used to mean a liquid, which may comprise a single constituent, or a mixture of more than one liquid, or a liquid or liquid mixture also comprising a suspension, or any of the foregoing further comprising a dissolved solute or solutes.

The term "heat" is used in its conventional sense to mean thermal energy content or warmth; the verb-form of the term, "to heat," is used herein to mean to transfer thermal energy, to increase the temperature of, to warm.

The term "hypothalamus" as used herein is meant to include the anatomical region of the brain termed in standard neuroanatomical usage the hypothalamus, but is not meant to be strictly limited to this neuroanatomical region. As used herein, the term "hypothalamus" is meant to include the brain regions generally accepted as being important in the regulation of body temperature in warm-blooded animals, particularly the pre-optic and suprachiasmatic nuclei of the hypothalamus, including neighboring areas of the brain such as the septum that have been found to be important in thermoregulation.

By the term "hyperthermia" is meant the condition of higher-than-normal body temperature in a warm-blooded animal. Locally increased temperature is termed "regional hyperthermia." Preferably, temperature in hyperthermia is raised at least about 1° C. to about 3° C. (that is, raised at least to about 38° C. to about 40° C.), more preferably temperature in hyperthermia is raised at least about 1° C. to about 5° C. (that is, raised at least to between about 38° C. to about 42° C.), or most preferably, temperature in hyperthermia is raised at least about 1° C. to about 7° C. (that is, raised at least to between about 38° C. to about 44° C.).

By the term "hypothermia" is meant the condition of lower-than-normal body temperature in a warm-blooded animal, that is, a reduction in, or lowering of, body temperature in an animal. Preferably, body temperature in hypothermia is lowered by at least about 2° C. to about 3° C. (that is, to between about 34° C. to about 35° C.), or more preferably, by at least about 3° C. to about 5° C. (that is, to between about 32° C. to about 34° C.), most preferably by at least about 5° C. (that is, to below about 32° C.).

The terms "nasal passage" and "nasal passages" are used herein to include the nostrils and to mean the anatomical regions connecting the nostrils with the sinuses of the skull.

The term "object" as used herein includes apparati, devices, probes, catheters, tubes, solid objects without cavities or passages, and objects with cavities or passages.

The term "oral passage" is meant herein to include the mouth and throat, and the opening connecting the oral cavity with the nasal passages behind the palate.

By the term "physiological cooling response" is meant the physiological and behavioral responses of an animal to warming, or to stimuli that usually accompany warming, usually effective to cool the animal. Responses that are usually effective to cool an animal are effective to rid the animal of excess heat or to reduce the body temperature of the animal, and may include, but are not limited to sweating, peripheral vasodilatation, panting, drooling, licking, and repositioning the body.

By the term "physiological warming response" is meant the physiological and behavioral responses of an animal to exposure to cold, or to stimuli that usually accompany cold, usually effective to warm the animal. Responses that are usually effective to warm an animal are effective to raise the body temperature of the animal, and may include, but are not limited to shivering, non-shivering thermogenesis, changes in blood flow, and repositioning the body.

Methods and Apparatus for Inducing Hypothermia

Figure 5:
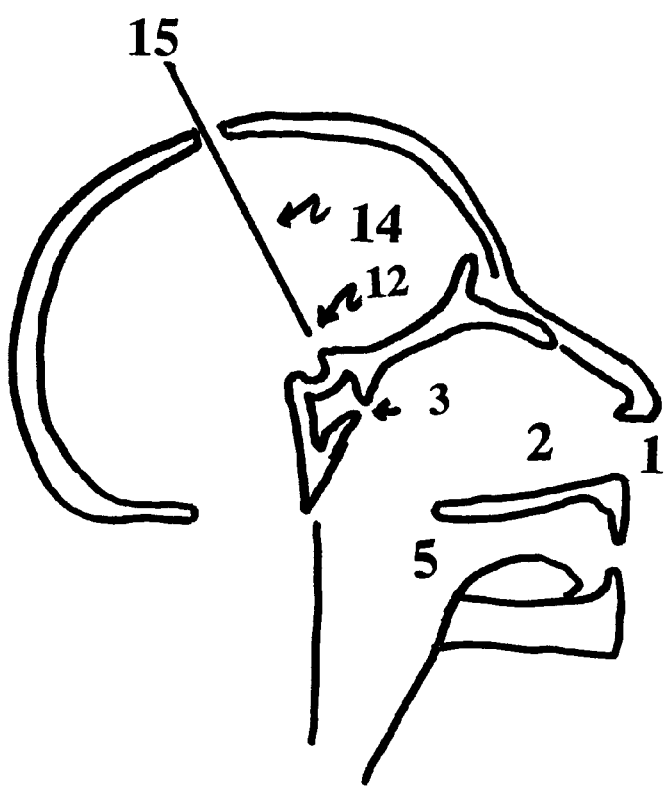
FIG. 5 is a cross-sectional view of a human head, showing placement of temperature-modulating means into the hypothalamic region of the brain.
Figure 6:
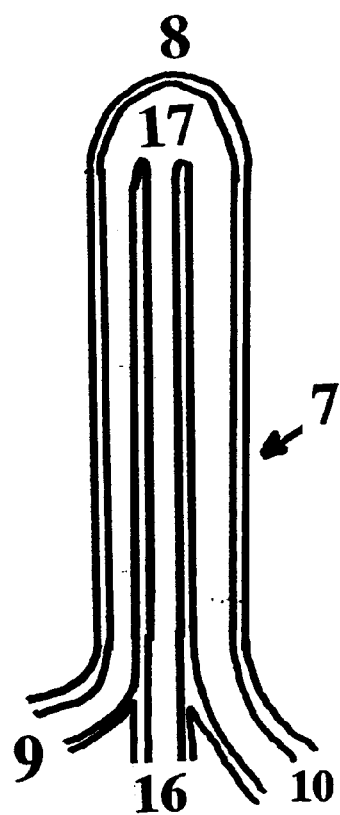
FIG. 6 is a cross-sectional view of a three-lumen catheter for mixing fluids to produce temperature-modulation near the tip.

Warming the hypothalamus 4 by direct application of heat, via a probe 14 placed in or near the hypothalamus, as shown in FIG. 5, or by direction of energy to the hypothalamus 4 will cause the hypothalamus to respond as if body temperature had risen, that is, by acting to lower body temperature in an attempt to restore body to normal. This hypothalamic response will continue as long as the temperature of the hypothalamus is maintained above its set point. Thus, where hypothermia is indicated for a desired therapeutic effect, warming the hypothalamus can be useful by inducing hypothermia, or by enhancing the effects of other methods for inducing hypothermia applied in conjunction with hypothalamic warming.

It is known that the hypothalamus 4 in humans is located near to the sphenoid sinus 3, a sinus which is accessible from the outside of a person via nasal passages 2 and the nostrils 1 and via the oral passage 5. A novel aspect of the present invention is the recognition that application of heat to the sphenoid sinus will warm the hypothalamus and cause a physiological cooling response. Warming of the sphenoid sinus will warm the hypothalamus of a person with normal blood flow but will not greatly warm other brain regions. Modeling suggests that the temperature near to a heat source in a well-perfused brain rises significantly only at the points nearest the heat source. Thus, application of heat to a nasal passage, sinus or directly to the hypothalamus will have only local direct effects on brain temperature, will not significantly raise temperature in other, more distal, brain regions, and will lead to global hypothermia.

The exact parameters of warming a nasal passage, sinus or hypothalamus, or combinations of these, may vary, as will be appreciated by those skilled in the art of medical practice, but will necessarily involve providing a warming means, applying said warming means so as to warm the hypothalamus or sinus or nasal passages, or combinations of these, to between about 38° C. and about 50° C. As said warming means is being applied, compounds may be introduced into a nasal passage or sinus. In some cases, it may be desirable as well to apply cooling measures to the animal, such as blowing air across exposed skin, applying cold dressings to exposed skin, and so forth. However, moderate cooling measures, if any, are preferred, since lowering the skin temperature will raise the hypothalamic temperature setpoint. For this reason, it may be advantageous to warm portions of the skin in order to lower the hypothalamic set-point and so aid in maintaining a lowered body temperature.

Description of Apparatus for Inducing Hypothermia

Heat may be applied to a nasal passage or a sinus or to a nasal passage and a sinus through the breathing of a warm gas, such as air mixed with steam or water mist (in a ratio of approximately 0% to 40% by volume) at a temperature between about 38° C. and about 50° C., although other temperatures may also be effective. Preferred temperatures are between about 38° C. and 43° C. This gas may be supplied, for example, to a nasal passage via a hollow tube 6, of a size smaller than a human nostril. Tubes effective for this purpose are approximately 0.1" to approximately 0.5" in outer diameter, may be thin-walled or thick-walled, and may be made, for example, of Tygon tubing. This tube may be inserted a short distance (for example, less than 0.5") into a nasal passage, or may be inserted farther into a nasal passage (for example, approximately 1" or more). Care must be taken that the animal breathes sufficient oxygen for health, and that sensitive nasal tissue is not scalded. If higher temperature gases are used, or higher fractions of steam or other warm gas, then smaller diameter tubes which do not fully occlude the nostril and so allow passage of air into the nasal passage are preferred. If lower temperature gases, nearer to 38° C. than 50° C., are used, then larger diameter tubing which occludes the nostril may be used.

Similarly, heat may be applied to a sinus, preferably the sphenoid sinus, through direction of a heated gas such as air mixed with steam via a tube or catheter 7. This heated gas may be air mixed with steam (in a ratio of approximately 0% to 40% by volume) at a temperature between about 38° C. and about 50° C., although other temperatures may also be effective. Preferred temperatures are between about 38° C. and 43° C. This gas may be supplied, for example, to a sinus by a hollow tube with an outside diameter of between about 0.05" and about 0.25". This hollow tube may be thin-walled or thick-walled, and is made, for example, of about 10 cm of flexible tubing with a smooth 4 mm curve at the distal end. This tube may be inserted through a nostril or through the mouth and oral cavity to gain access to a nasal passage above the palate and then into a sinus. Insertion of this tube may be aided by a guide tube, a guide wire, or other implement. Care must be taken that sensitive tissue is not scalded or damaged during insertion. Insertion of this tube is preferably done using methods in common use for introduction of drain tubes into inflamed sinuses for the purpose of draining accumulated fluids.

A nasal passage or sinus may be also warmed by an apparatus which is itself heated and delivers heat. One such apparatus comprises a closed-ended flexible tube containing warm gases, such as the mixtures of steam and air, or other warm gases, or preferably containing a warm fluid, such as warm saline or other liquid, capable of being introduced into a nasal passage or sinus. Warm fluids are preferred over warm gases in this embodiment because their higher heat capacity and greater mass make them more effective to warm the tissue with which they are in contact. The temperature of said gas or fluid may be between about 38° F. and 50° C. Preferred temperatures are between about 38° C. and 43° C. Such an apparatus can be a tube with a single lumen and a distal end blocked to prevent outflow of hot gases or fluids. In a preferred embodiment, this apparatus comprises a tube with at least two inner lumens, at least one for inflow of warm fluid or gas 9, at least one for outflow of warm fluid or gas 10, with a distal end of said tube blocked to prevent outflow of the warm fluid or gas enclosed 8. Constant flow of said warm fluid or gas is maintained to provide continuous heating to the nasal passage or sinus. In a preferred embodiment, said closed end is a distal end comprised of thinner wall thickness than the lateral wall of the apparatus. An effective thickness for the blocked distal end is between about 0.001" and about 0.05". In another preferred embodiment, said distal end is constructed of a thin flexible material, such as latex rubber or polyethylene of a thickness between about 0.001" and about 0.05" effective for transferring heat and capable of expanding or "ballooning out" to fill space surrounding it under application of internal positive pressure. This apparatus may be inserted through a nostril or through the mouth and oral cavity and then to a nasal passage above the palate and into a sinus. Insertion of this apparatus may be aided by a guide tube, a guide wire 11, or other implement. Care must be taken that sensitive tissue is not scalded or damaged during insertion. Insertion of this apparatus is preferably done using methods in common use for introduction of drain tubes into inflamed sinuses for the purpose of draining accumulated fluids.

Another such apparatus effective to warm a nasal passage or sinus comprises an electrical warming device 12 attached at an end of a flexible tube, rod or catheter capable of being introduced into a nasal passage or sinus. Said electrical warming device may be a thermocouple, Peltier device, electrical heating element, or the like. In a preferred embodiment the electrical warming is obtained by passing electrical current through an insulated coil of nichrome wire (30 to 36 AWG, coil outer diameter 0.04") connected to insulated copper or silver wires (26 to 30 gauge, twisted wire) insulated with a flexible insulating coating of an insulating material such as polyimide or epoxy. The heating element is preferably shaped in a helical coil with an outer dimension of about 0.08" diameter and contained inside an insulating coating. Effective temperatures at the heating element are between about 38° C. and about 50° C. Preferred temperatures are between about 38° C. and about 43° C. to provide warming of the nasal passage or sinus. In a preferred embodiment, a temperature sensor 13 is enclosed with the coil to provide temperature feedback to control the applied temperature. This apparatus may be inserted through a nostril or through the mouth and oral cavity and to a nasal passage above the palate and then into a sinus. Insertion of this apparatus may be aided by a guide tube, a guide wire, or other implement. Care must be taken that sensitive tissue is not scalded or damaged during insertion. Insertion of this apparatus is preferably done using methods in common use for introduction of drain tubes into inflamed sinuses for the purpose of draining accumulated fluids.

Heating of the hypothalamus directly may be accomplished by insertion of heated tubes or electrical devices, and other devices of similar effects, directly into the hypothalamus though surgical procedures. In some embodiments, preferred apparatus are not flexible tubes, but are made of medical grade stainless steel 14, of an outside diameter between about 0.01" and about 0.08". Alternatively, flexible wires may connect to heating elements placed in or near the hypothalamus. FIG. 5 illustrates one surgical approach for placement of a heating probe into the hypothalamus. Other approaches are suitable as well, including, for example, introducing probes or heating elements near or in the hypothalamus from surgical entry points at the side of the skull, or via a frontal approach. Electrical methods of heating are preferred over methods utilizing heated fluids or gases for this embodiment of the invention. Preferred electrical methods and apparatus include heating elements such as thermocouples, Peltier devices and resistive heating wires such as Nichrome wire provided at the tips of stainless steel rods or attached to flexible wires. In addition, the delivery of radio-frequency current is effective to warm the hypothalamus. Electrical stimulation of neurons in the hypothalamus is also effective to stimulate hypothalamic neurons to trigger a physiological cooling response.

Thermocouples, Peltier devices, resistive heating wires, and other electrical warming devices are provided with sources of electrical power, such as batteries, connected by wires or other suitable electrical connection. The electrical power source may be regulated (i.e. passively by a resistor or other passive control components, or actively, by control circuitry including feedback control circuits). Warming devices may also include temperature sensors. Such sensors may be used to report temperatures adjacent the sensors to clinical observers, and may be used to control the warming device as part of a control circuit or control apparatus.

Thermocouples, Peltier devices, resistive heating wires, stimulating electrodes, and other electrical devices may be implanted within the skull of an animal. Such implantation may be within the brain itself, including within the hypothalamus; may be near the hypothalamus, outside the brain but within the dura mater; or may be near the hypothalamus outside the dura mater.

Devices for modulating body temperature by modifying hypothalamic temperature that are placed within the skull of the animal may remain within the skull of the animal for an extended period of time. The duration of such an extended period of time will vary depending upon the type and stage of cancer to be treated, the condition of the patient, type of cancer treatment used in conjunction with modulation of body temperature, and other criteria. The durations of such extended periods of time may be up to 3 days; or up to 7 days; or up to 15 days; or up to one month; or more than one month depending upon the criteria discussed and the response of the animal to the course of treatment.

Heating of the hypothalamus may be effected by infrared radiation directed to the hypothalamus, such as infrared radiation delivered to the inside of the sphenoid sinus or nasal passage by an infrared source such as a heated coil inside a thermally cooled jacket. In this embodiment, warming of the hypothalamus is effected by either infrared radiation alone, or by infrared radiation along with heat delivered to the hypothalamus by conduction through intervening tissue. Other forms of radiation and radiative heating are suitable as well.

Physiological cooling responses may be initiated by introduction of chemical compounds into a nasal passage and a sinus, at the same time as warm gases or heat is introduced, or in the absence of said heating. Compounds such as melatonin, capsaicin and other compounds are effective to induce a physiological cooling response. Effective concentrations of melatonin are between about 0.1 nM and about 100 nM. Effective concentrations of capsaicin are between about 1 nM and about 1 $\mu$M.

Local warming of cancerous tissue, during hypothermia, may be accomplished by application of a heated probe, such as probe 14 (described above for use in the hypothalamus) shown in FIG. 5, or application of heated fluids, hot gas (such as warm or hot air, or other gases), heating pads, electric heaters, tubes or containers containing heated fluids, or the like. Alternatively, thermal radiation, whether infrared, microwave, or other radiation, may be directed to the cancerous tissue to maintain its temperature near to, or above, normal body temperature while the rest of the body is hypothermic. Similarly, ultrasound radiation may be applied to maintain the temperature of the cancerous tissue near to, or above, normal body temperature while the rest of the body is hypothermic. That is, during hypothermia, when substantially all of the rest of the animal experiences reduced body temperature, the temperature of the cancerous tissue is maintained at a temperature of between about 35° C. and about 44° C., preferably between about 35° C. to about 40° C., and most preferably between about 36° C. to about 38° C. In yet other embodiments of the method, the cancerous tissue is maintained at a temperature between about 38° C. and about 44° C.

When the treatment includes chemotherapy, standard chemotherapy regimens known in the art are applied. Chemotherapy regimens may use standard or nonstandard chemotherapy drugs including as methotrexate, 5-fluoruracil, doxorubicin, cisplatin, taxol, and other drugs, individually or in combination. The dosage of drug or drugs used can depend upon various factors, such as the mode of administration, species, age, weight and individual state. The doses to be administered daily are about 0.05 to about 100 mg/kg body weight per individual component. The amount of the particular active material per form of administration can be from about 5 to about 1000 mg.

When the treatment includes radiation treatment, standard radiation therapy regimens known in the art are applied. Typical radiotherapy regimens include exposure of cancerous tissue to ionizing radiation daily (e.g., five times per week) for about 5 or more weeks, where both the length of treatment and the total dosage of radiation are dictated by the tumor size, location, tumor type, and other factors known in the art. For example, treatment regimens for small microscopic tumors typically include daily exposure of the tumor to ionizing radiation for approximately 5 weeks with a cumulative ionizing radiation dosage of about 4500–5000 rads. Treatment regimens for larger tumors as well as tumors located in the head and neck typically are extended to 8 or more weeks and can employ a cumulative ionizing radiation dosage of about 7400 or more rads.

EXAMPLE 1

This example illustrates the use of warm gas to warm a nasal passage, sinus and hypothalamus. A mixture of 25% steam and 75% air (v/v) is combined in a chamber to which are connected two flexible Tygon tubes of outer diameter 0.125" which are inserted into the nostrils of a human subject. The human subject breathes the warm gas mixture normally through the nose. In approximately 5 minutes, the subject begins to sweat. This physiological cooling response is effective to lower the animal's body temperature.

EXAMPLE 2

This example illustrates the use of a warming tube inserted into the sphenoid sinus via a nostril. The warming tube is a flexible tube with two lumens. Warm saline (43° C.) at a pressure head of 50 cm flows towards the distal end of the warming tube in one lumen, and returns via the other lumen at a pressure head of 0 cm. The distal end of the warming tube opens into and is enclosed by a distensible balloon made of latex rubber (wall thickness 0.005") which acts to direct the warm fluid flow from the inflow tube to the outflow tube. A stainless steel guide wire 11 cm in length with a shapeable tip, gently curved for the last 4 mm, is inserted into the guidewire lumen and is used to direct the distal end of the warming tube into the sphenoid sinus. The latex rubber balloon at the distal end of the warming tube expands into the sphenoid sinus once the outflow pressure head becomes positive following partial occlusion of the outflow. The circulation of warm saline inside the balloon warms the sphenoid sinus, the skull and the brain structures adjacent the sphenoid sinus, including the hypothalamus, and the animal begins to sweat. This physiological cooling response is effective to lower the animal's body temperature.

EXAMPLE 3

This example illustrates the use of warm gas to warm a nasal passage, sinus and hypothalamus and the additional use of compounds effective to increase the hypothermia induced by warming a nasal passage, sinus and hypothalamus. A mixture of 25% steam and 75% air (v/v) with added melatonin and capsaicin is combined in a chamber to which is connected a two-lumen flexible polyethylene extrusion of outer diameter 4 mm which is inserted into the nostrils of a human subject. The melatonin and capsaisin are added to the mixing chamber via an atomizer spray as a solution in saline (0.9% sodium chloride) of 10 nM melatonin, 1 mg/mL bovine serum albumin and 100 nM capsaicin. The human subject breathes the warm gas mixture normally through the nose. In approximately 5 minutes, the animal begins to sweat. This physiological cooling response is effective to lower the animal's body temperature.

EXAMPLE 4

This example illustrates the use of direct heating in the hypothalamus to produce a physiological cooling response. Standard imaging techniques are used to image the brain of the human patient prior to any surgical procedures. Accepted neurosurgical procedures are followed when exposing the skull and drilling a small hole in the skull 15, inserting a guide-tube under stereotactic control. After local anesthetic is applied, a Leksell stereotactic frame is applied to the head of a human patient and an incision in the scalp is made, exposing the skull. A single 3-mm twist drill hole is made in the exposed skull anterior to the coronal suture approximately 2 cm from the midline. The dura is penetrated with a sharp probe and a 1.1 mm guide tube is stereotactically placed in the cerebrum so that the tip is within 1 cm of the anterior hypothalamus. A sterile microelectrode is attached to a hydraulic microdrive and the tip of the electrode is advanced down the guide tube until it protrudes from the guide tube into the pre-optic/anterior hypothalamic region of the hypothalamus. Monopolar radio-frequency stimulation is imposed. The ground is 3.5 inch, 18-gauge needle placed into a deltoid muscle. Measurement of the temperature of the electrode tip is used to control the power such that the temperature rise at the electrode tip is limited to 1° C. The patient begins sweating and vasodilation begins within 5 minutes, and the patient's body temperature begins to drop.

EXAMPLE 5

This example illustrates the use of a chemical warming device to produce a physiological cooling response in a human patient. This chemical warming device comprises a guide wire, fluid reservoirs and pumps, and a flexible polyethylene tube of outer diameter 0.1" with three lumens: two of 0.03" inner diameter, one of 0.015" inner diameter 16. The distal end of this tube is occluded with all three lumens opening into a common mixing chamber 17 of 0.08" diameter and 0.04" breadth. Distilled water flows in both of the larger diameter lumens, one lumen serving for inflow of distilled water, the other for outflow. The third, smallest lumen contains an aqueous mixture of 100 mM KOH. Liquid in all three tubes is maintained at a pressure less than ambient pressure to insure that, in the event of failure, no liquid will escape into the patient. Liquid flow is maintained by a siphon effect, with the two inflow reservoirs and one outflow reservoir being situated below the level of the patient's head. KOH solution is introduced into the mixing chamber by increasing the flow rate of that liquid (with a concomitant increase in outflow rate). This causes the KOH solution to mix with and to be diluted in the distilled water, thereby releasing heat in the region where mixing occurs. The chemical warming device is used in the following manner: the distal end of the chemical warming device is directed near to the sphenoid sinus as distilled water is flowing through the tube; when the tube is positioned as desired, KOH solution flow is initiated, with an increase in the fluid outflow rate as well to insure adequate and appropriate removal of fluid from the mixing chamber situated in the distal end of the tube, thereby heating the tip region of the chemical warming device, warming a sinus, and inducing a physiological cooling response.

EXAMPLE 6

This example illustrates the induction of hypothermia by directing heat to the hypothalamus as therapy for cancer. Hypothermia may be induced by any method, such as the methods of Examples 1 through 5, in a patient suffering from cancer that is susceptible to metastasis. In this example, hypothermia is induced by the method of Example 4. Heating is chronically maintained in the hypothalamus for as long as the probe is in place within the skull of the patient. Induction of hypothermia is effective to reduce the extent of metastasis of the cancer, thereby slowing the progression of the disease in the patient.

EXAMPLE 7

This example illustrates the induction of hypothermia by directing heat to the hypothalamus as an adjunct to cancer radiation therapy. Hypothermia may be induced by any method, such as the methods of Examples 1 through 5, in a patient suffering from cancer that is susceptible to radiation treatment. In this example, hypothermia is induced by the method of Example 4. Heating of the hypothalamus, effective to induce hypothermia, is maintained for a period of five hours, beginning prior to the initiation of each radiation therapy session. Induction of hypothermia is effective to enhance the effectiveness of the radiation therapy, thereby aiding the treatment of the disease in the patient.

EXAMPLE 8

This example illustrates the induction of hypothermia by directing heat to the hypothalamus as an adjunct to cancer radiation therapy. Hypothermia may be induced by any method, such as any of the methods of Examples 1 through 5, in a patient suffering from skin cancer that is susceptible to radiation treatment. In this example, hypothermia is induced by the method of Example 4. Heating of the hypothalamus, effective to induce hypothermia, is maintained for a period of five hours, beginning prior to the initiation of each radiation therapy session. The cancerous tissue in the patient is maintained at normal body temperature by the application to the cancerous skin of a warm pad slightly larger in area than the area of cancerous tissue. The pad is heated by circulating warm water within the pad. Induction of hypothermia while maintaining the cancerous tissue at a temperature between 36° C. and 38° C., is effective to enhance the effectiveness of the radiation therapy, thereby aiding the treatment of the disease in the patient.

EXAMPLE 9

This example illustrates the induction of hypothermia by directing heat to the hypothalamus as an adjunct to cancer radiation therapy. Hypothermia may be induced by any method, such as any of the methods of Examples 1 through 5, in a patient suffering from prostate cancer that is susceptible to radiation treatment. In this example, hypothermia is induced by the method of Example 4. Heating of the hypothalamus, effective to induce hypothermia, is maintained for a period of five hours, beginning prior to the initiation of each radiation therapy session. The cancerous prostate tissue in the patient is maintained at normal body temperature by the direction of ultrasound energy to the cancerous prostate. The prostate is warmed by an ultrasound probe inserted via the urethra, by the method of Andrus et al., U.S. Pat. No. 5,895,356. Induction of hypothermia while maintaining the cancerous prostate at a temperature between 36° C. and 38° C. is effective to enhance the effectiveness of the radiation therapy, thereby aiding the treatment of the disease in the patient.

EXAMPLE 10

This example illustrates the induction of hypothermia by directing heat to the hypothalamus as an adjunct to cancer chemotherapy. Hypothermia may be induced by any method, such as any of the methods of Examples 1 through 5, in a patient suffering from prostate cancer that is susceptible to chemotherapy treatment. The method of Example 4 is used to warm the hypothalamus of a patient undergoing chemotherapy for prostate cancer, effective to induce hypothermia in the patient during the time the patient receives his chemotherapy treatment. Five hours after the chemotherapy treatment session is completed, the hypothalamic warming is curtailed, and the patient's body temperature returns to normal. The chemotherapy is much more effective than such treatment in the absence of the hypothermia.

EXAMPLE 11

This example illustrates the induction of hypothermia by directing heat to the hypothalamus as an adjunct to cancer chemotherapy. Hypothermia may be induced by any method, such as any of the methods of Examples 1 through 5, in a patient suffering from prostate cancer that is susceptible to chemotherapy treatment. The method of Example 4 is used to warm the hypothalamus of a patient undergoing radiation therapy for prostate cancer. The prostate is warmed by an ultrasound probe inserted via the urethra, by the method of Andrus et al., U.S. Pat. No. 5,895,356. The prostate itself is maintained at a temperature between 36° C. and 38° C. while the temperature of the rest of the patient is reduced to below 33° C. Five hours after the chemotherapy, the hypothalamic warming is curtailed, and the patient's body temperature returns to normal. The chemotherapy is much more effective than such treatment in the absence of the temperature differential between the cancerous tissue and the rest of the body.

EXAMPLE 12

Figure 7:
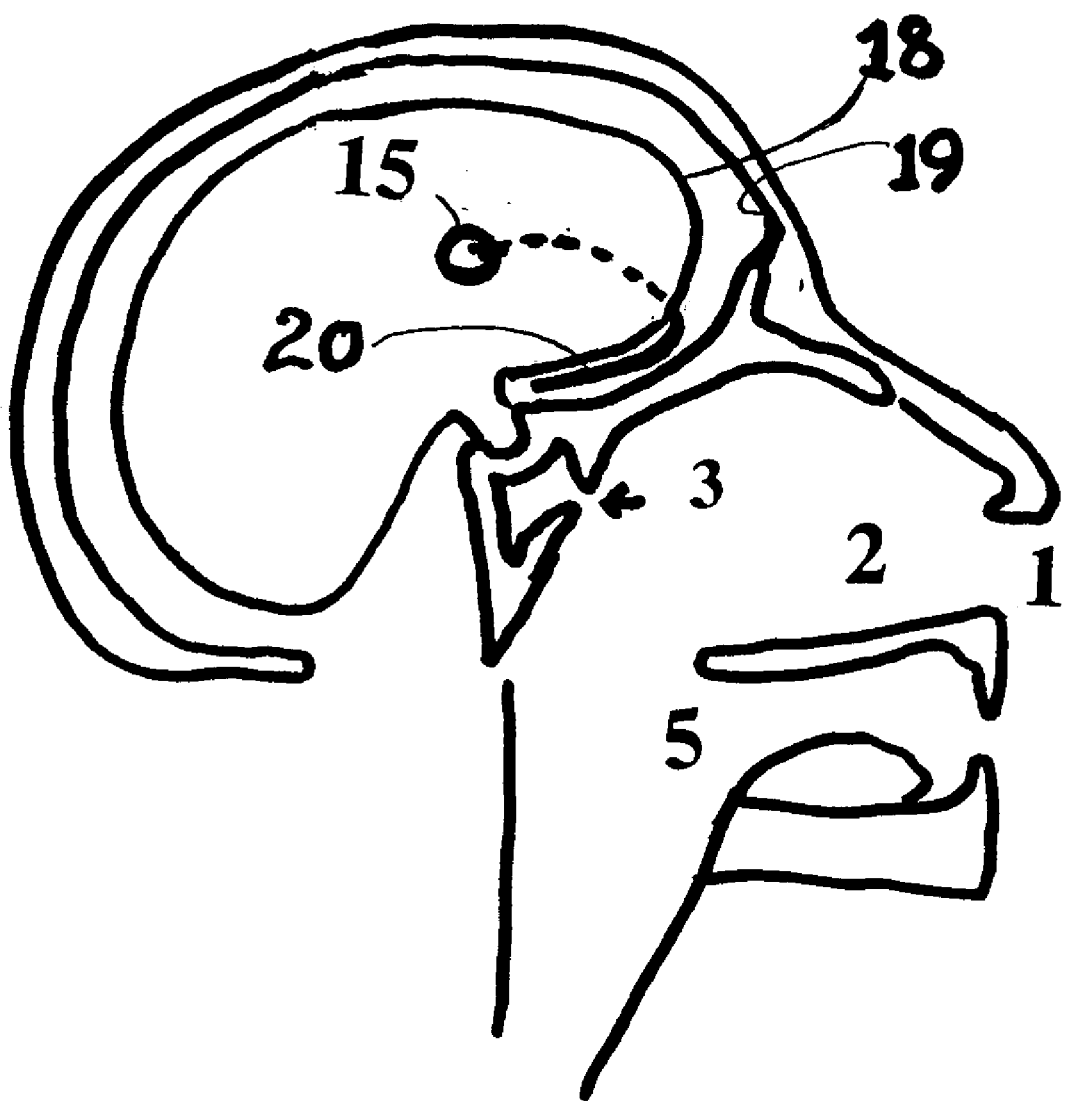
FIG. 7 is a schematic illustration of a cross-sectional view of a human head, showing placement of temperature-modulating means between the skull and the dura mater near to the hypothalamic region of the brain.

This example illustrates the placement of a chronic implant to provide local heating near to the hypothalamus to produce a physiological cooling response. Standard imaging techniques are used to image the brain of the human patient prior to any surgical procedures. Accepted neurosurgical procedures are followed when exposing the skull and drilling a small hole in the skull 15, inserting a guide-tube under stereotactic control. After local anesthetic is applied, a Leksell stereotactic frame is applied to the head of a human patient and an incision in the scalp is made, exposing a region of the left side of the skull. A single 3-mm twist drill hole is made in the exposed skull at a position superior to the temple approximately 2 cm inferior to the crown of the skull and approximately 1 cm posterior to the orbit. Care is taken that the dura mater 18 is not penetrated or damaged during the procedure. A sterile thermocouple with attached wire leads threaded inside a flexible tube 20 is advanced into the hole between the inside of the skull 19 and the dura mater 18 (flexible tube 20 is shown as a dotted line where it would be seen as behind the dura mater 18 in the view shown in FIG. 7). The wire leads are attached to a voltage source and voltage regulator. The thermocouple is advanced to a position near the hypothalamus outside the dura mater 18. A schematic illustration of the placement of such a device is shown in FIG. 7. After placement of the device, the hole 15 in the skull is filled with surgical cement. Voltage is applied to the thermocouple via the leads, effective to heat the thermocouple and to heat the hypothalamus of the patient. The patient's body temperature begins to drop. Patient response and temperature are monitored. If necessary or desired, voltage adjustments are made to provide the desired hypothalamic heating. The incision is closed, with the leads and voltage source lying between the skull and skin of the patient. The implant is left in place for an extended period of several weeks to several months effective to provide chronic hypothalamic warming for long-term hypothermia.

Methods and Apparatus for Inducing Hyperthermia

Cooling the hypothalamus 4 by direct application of cold temperatures, via a probe 14 placed in or near the hypothalamus, as shown in FIG. 5, or by any means of removing heat energy from the hypothalamus 4 will cause the hypothalamus to respond as if body temperature had fallen; that is, the hypothalamus will respond by acting to raise body temperature in an attempt to restore the body to normal. This hypothalamic response will continue as long as the temperature of the hypothalamus is maintained below its set point. Thus, where hyperthermia is indicated for a desired therapeutic effect, cooling the hypothalamus can be useful by inducing hyperthermia, or by enhancing the effects of other methods for inducing hyperthermia applied in conjunction with hypothalamic cooling.

It is known that the hypothalamus 4 in humans is located near to the sphenoid sinus 3, a sinus which is accessible from the outside of a person via nasal passages 2 and the nostrils 1 and via the oral passage 5. A novel aspect of the present invention is the recognition that application of cold to the sphenoid sinus will cool the hypothalamus and cause a physiological warming response. Cooling of the sphenoid sinus will cool the hypothalamus of a person with normal blood flow but will not greatly cool other brain regions. Modeling suggests that the temperature near to a heat source in a well-perfused brain generally rises significantly only at the points nearest the heat source. Thus, application of cold temperatures to a nasal passage, sinus or directly to the hypothalamus will have only local direct effects on brain temperature, will not significantly lower temperature in other, more distal, brain regions, and will lead to global hyperthermia.

The exact parameters of cooling a nasal passage, sinus or hypothalamus, or combinations of these, may vary, as will be appreciated by those skilled in the art of medical practice, but will necessarily involve providing a cooling device, applying said cooling device so as to cool the hypothalamus or sinus or nasal passages, or combinations of these, to between about 37° C. and about 20° C. As said cooling device is being applied, compounds may be introduced into a nasal passage or sinus. In some cases, it may be desirable as well to apply warming measures to the animal, such as blowing warm air across exposed skin, applying warm dressings to exposed skin, and so forth. However, moderate external warming measures, if any, are preferred, since raising the skin temperature will lower the hypothalamic temperature set-point. For this reason, it may be advantageous to cool portions of the skin in order to raise the hypothalamic set-point and so aid in maintaining a raised body temperature.

Description of Apparatus for Inducing Hyperthermia

Cold may be applied to a nasal passage or a sinus or to a nasal passage and a sinus through the breathing of a cool gas, such as cold air, or cold air mixed with a cold inert gas or mist (in a ratio of approximately 0% to 40% by volume) at a temperature between about 22° C. and about 2° C., although other temperatures may also be effective. The mist may comprise water mist, or may comprise water and alcohol, alcohol alone, or other readily evaporating liquid, to enhance heat absorption. Preferred temperatures are between about 18° C. and 5° C. This gas may be supplied, for example, to a nasal passage via a hollow tube 6, of a size smaller than a human nostril. Tubes effective for this purpose are approximately 0.1" to approximately 0.5" in outer diameter, may be thin-walled or thick-walled, and may be made, for example, of Tygon tubing. This tube may be inserted a short distance (for example, less than 0.5") into a nasal passage, or may be inserted farther into a nasal passage (for example, approximately 1" or more). Care must be taken that the animal breathes sufficient oxygen for health, and that sensitive nasal tissue is not damaged.

Similarly, cold may be applied to a sinus, preferably the sphenoid sinus, through direction of a cooled gas such as air mixed with mist via a tube or catheter 7. The mist may comprise water mist, or may comprise water and alcohol, alcohol alone, or other readily evaporating liquid, to enhance heat absorption. This cooled gas may be air mixed with mist (in a ratio of approximately 0% to 40% by volume) at a temperature between about 22° C. and about 2° C., although other temperatures may also be effective. Preferred temperatures are between about 18° C. and 5° C. This gas may be supplied, for example, to a sinus by a hollow tube with an outside diameter of between about 0.05" and about 0.25". This hollow tube may be thin-walled or thick-walled, and is made, for example, of about 10 cm of flexible tubing with a smooth 4 mm curve at the distal end. This tube may be inserted through a nostril or through the mouth and oral cavity to gain access to a nasal passage above the palate and then into a sinus. Insertion of this tube may be aided by a guide tube, a guide wire, or other implement. Care must be taken that sensitive tissue is not scalded or damaged during insertion. Insertion of this tube is preferably done using methods in common use for introduction of drain tubes into inflamed sinuses for the purpose of draining accumulated fluids.

A nasal passage or sinus may be also cooled by an apparatus which is itself cooled and removes heat. One such apparatus comprises a closed-ended flexible tube containing cold gases, such as the mixtures of water mist and air, or other cold gases, or preferably containing a cold fluid, such as cold saline or other liquid, capable of being introduced into a nasal passage or sinus. Cold fluids are preferred over cold gases in this embodiment because their higher heat capacity and greater mass make them more effective to cool the tissue with which they are in contact. The temperature of said gas or fluid may be between about 22° C. and 2° C., although other temperatures are also suitable. Preferred temperatures are between about 18° C. and 5° C. Such an apparatus can be a tube with a single lumen and a distal end blocked to prevent outflow of hot gases or fluids. In a preferred embodiment, this apparatus comprises a tube with at least two inner lumens, at least one for inflow of cold fluid or gas 9, at least one for outflow of fluid or gas 10, with a distal end of said tube blocked to prevent outflow of the cold fluid or gas enclosed 8. Constant flow of said cold fluid or gas is maintained to provide continuous cooling to the nasal passage or sinus. In a preferred embodiment, said closed end is a distal end comprised of thinner wall thickness than the lateral wall of the apparatus. An effective thickness for the blocked distal end is between about 0.001" and about 0.05". In another preferred embodiment, said distal end is constructed of a thin flexible material, such as latex rubber or polyethylene of a thickness between about 0.001" and about 0.05" effective for transferring heat and capable of expanding or "ballooning out" to fill space surrounding it under application of internal positive pressure. This apparatus may be inserted through a nostril or through the mouth and oral cavity and then to a nasal passage above the palate and into a sinus. Insertion of this apparatus may be aided by a guide tube, a guide wire 11, or other implement. Care must be taken that sensitive tissue is not damaged during insertion. Insertion of this apparatus is preferably done using methods in common use for introduction of drain tubes into inflamed sinuses for the purpose of draining accumulated fluids.

Another such apparatus effective to cool a nasal passage or sinus comprises an electrical cooling device 12 attached at an end of a flexible tube, rod or catheter capable of being introduced into a nasal passage or sinus. Said electrical cooling device may be a Peltier device or other electrical cooling element. In a preferred embodiment the electrical cooling is obtained by passing electrical current through a Peltier device. The Peltier device may be located at the tip of the cooling device 12 or may be located distal to the tip and heat withdrawn form the tip by the cooling device via a heat pipe. Small Peltier devices may be obtained commercially, such as the OptoTEC™ (e.g., OT 0.8-18-FO) manufactured by Melcor (1040 Spruce Street, Trenton N.J. 08648) or custom made by commercial suppliers. The tip of a probe may be cooled via a heat pipe that connects the tip of a probe to a cooling element such as a Peltier device. Heat pipes are described, for example, in U.S. Pat. No. 5,190,539 to Fletcher et al. and U.S. Pat. No. 5,417,686 to Peterson et al.

An electrical cooling probe may be covered with a flexible coating of an insulating material such as polyimide or epoxy. Effective temperatures at the cooling element are between about 22° C. and about 2° C. Preferred temperatures are between about 18° C. and about 5° C. to provide cooling of the nasal passage or sinus. In a preferred embodiment, a temperature sensor 13 is enclosed with the coil to provide temperature feedback to control the applied temperature. This apparatus may be inserted through a nostril or through the mouth and oral cavity and to a nasal passage above the palate and then into a sinus. Insertion of this apparatus may be aided by a guide tube, a guide wire, or other implement. Care must be taken that sensitive tissue is not damaged during insertion. Insertion of this apparatus is preferably done using methods in common use for introduction of drain tubes into inflamed sinuses for the purpose of draining accumulated fluids.

In a preferred embodiment, cooling is directed to the hypothalamus, cooling the hypothalamus and producing a therapeutic warming response. Such cooling may be by placement of a cool probe near to the hypothalamus, or placement of a cool probe in the hypothalamus, or placement, near to or in the hypothalamus, of a probe capable of being cooled by electrical means, by fluid flow, by conduction of heat away from the hypothalamus via the probe, or other cooling means. Thus, placement of a cooling device near to, or in, the hypothalamus comprises a means for directing cooling to the hypothalamus. It will be understood by those of skill in the art that heat conductive probes, heat pipes, heat conductive fluids, and other devices known in the art are also effective to direct cooling to the hypothalamus. In a preferred embodiment, a cooling device is operably connected to a heat conductive probe, the probe being adapted for placement near to or in the hypothalamus.

Cooling of the hypothalamus directly may be accomplished by insertion of cooled tubes, electrical cooling devices, probes enclosing heat pipes connecting the tip of the probe to cooling devices, and other devices of similar effects, directly into the hypothalamus though surgical procedures. Preferred apparatus are not flexible tubes, but are made of medical grade stainless steel 14, of an outside diameter between about 0.01" and about 0.08". Effective temperatures at the cooling element are between about 36.5° C. and about 5° C. Preferred temperatures are between about 35° C. and about 25° C. FIG. 5 illustrates one surgical approach for placement of a heating probe into the hypothalamus, in which an incision is made in the scalp of a patient, a burr hole made in the skull, a further incision made in the dura mater, and a heating probe introduced into the brain of the patient, with the heating element near to or within the hypothalamus of the patient. Other approaches are suitable as well, including, for example, introducing probes or cooling elements near or in the hypothalamus from surgical entry points at the side of the skull, or via a frontal approach. Probes enclosing cooling fluids or gases (including heat pipes connected to cooling elements) are preferred. Electrical methods of cooling may also be employed in the practice of this embodiment of the invention. Preferred electrical methods and apparatus include cooling elements such as Peltier devices provided at the tips of stainless steel rods or attached to flexible wires. Electrical stimulation of neurons in the hypothalamus is also effective to stimulate hypothalamic neurons to trigger a physiological cooling response.

Peltier devices and other electrical cooling devices are provided with sources of electrical power, such as batteries, connected by wires or other suitable electrical connection. The electrical power source may be regulated (i.e. passively by a resistor or other passive control components, or actively, by control circuitry including feedback control circuits). Cooling devices may also include temperature sensors. Such sensors may be used to report temperatures adjacent the sensors to clinical observers, and may be used to control the cooling device as part of a control circuit or control apparatus.

Peltier devices and other cooling devices may be implanted within the skull of an animal. Such implantation may be within the brain itself, including within the hypothalamus; may be near the hypothalamus, outside the brain but within the dura mater; or may be near the hypothalamus outside the dura mater. Such devices may remain within the skull of the animal for an extended period of time. The duration of such an extended period of time will vary depending upon the type and stage of cancer to be treated, the condition of the patient, type of cancer treatment used in conjunction with modulation of body temperature, and other criteria. The durations of such extended periods of time may be up to 3 days; or up to 7 days; or up to 15 days; or up to one month; or more than one month depending upon the criteria discussed and the response of the animal to the course of treatment.

Physiological cooling responses may be initiated by introduction of chemical compounds into a nasal passage and a sinus, at the same time as cold gases or cooling fluids are introduced, or in the absence of said cooling.

Local warming of cancerous tissue, during hyperthermia induced by cooling of the hypothalamus, may also be performed in the practice of the invention. Such local warming of cancerous tissue may be accomplished by application of a heated probe, or application of heated fluids, hot gas (such as warm or hot air, or other gases), heating pads, electric heaters, tubes or containers containing heated fluids, or the like. Alternatively, thermal radiation, whether infrared, microwave, or other radiation, may be directed to the cancerous tissue to further increase its temperature while the rest of the body is rendered hyperthermic by cooling of the hypothalamus. Similarly, ultrasound radiation may be applied to increase the temperature of the cancerous tissue near to, or above, normal body temperature while the rest of the body is rendered hyperthermic by cooling of the hypothalamus.

When the treatment includes chemotherapy, standard chemotherapy regimens known in the art are applied while the patient is rendered hyperthermic by cooling of the hypothalamus. Chemotherapy regimens may use standard or nonstandard chemotherapy drugs including as methotrexate, 5-fluoruracil, doxorubicin, cisplatin, taxol, and other drugs, individually or in combination. The dosage of drug or drugs used can depend upon various factors, such as the mode of administration, species, age, weight and individual state. The doses to be administered daily are about 0.05 to about 100 mg/kg body weight per individual component. The amount of the particular active material per form of administration can be from about 5 to about 1000 mg.

When the treatment includes radiation treatment, standard radiation therapy regimens known in the art are applied while the patient is rendered hyperthermic by cooling of the hypothalamus. Typical radiotherapy regimens include exposure of cancerous tissue to ionizing radiation daily (e.g., five times per week) for about 5 or more weeks, where both the length of treatment and the total dosage of radiation are dictated by the tumor size, location, tumor type, and other factors known in the art. For example, treatment regimens for small microscopic tumors typically include daily exposure of the tumor to ionizing radiation for approximately 5 weeks with a cumulative ionizing radiation dosage of about 4500–5000 rads. Treatment regimens for larger tumors as well as tumors located in the head and neck typically are extended to 8 or more weeks and can employ a cumulative ionizing radiation dosage of about 7400 or more rads.

When the disease to be treated is an infectious or parasitic disease, drugs and other anti-infectious treatments, or anti-parasitic treatments may be applied along with hyperthermia. Such treatments are well known in the art. Infections may be viral, bacterial, fungal, parasitic or by other organisms. Thus, the treatment for an infectious disease will be selected from antibacterial therapy, antiviral therapy, antifungal therapy, parasitic, and other therapies, depending upon the type of disease to be treated.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains. All patents, patent applications and publications mentioned herein, both supra and infra, are incorporated by reference in their entirety.

EXAMPLE 13

This example illustrates the use of cold gas to warm a nasal passage, sinus and hypothalamus. A mixture of air and water/alcohol (1/1) mist is cooled in a chamber to a temperature of 5° C. to which are connected two flexible Tygon tubes of outer diameter 0.125" which are inserted into the nostrils of a human subject. The human subject breathes the cold gas mixture normally through the nose. In approximately 5 minutes, the subject begins to shiver. This physiological warming response is effective to raise the subject's body temperature.

EXAMPLE 14

This example illustrates the use of a cooling tube inserted into the sphenoid sinus via a nostril. The cooling tube is a flexible tube with two lumens. Cold saline (5° C.) at a pressure head of 50 cm flows towards the distal end of the warming tube in one lumen, and returns via the other lumen at a pressure head of 0 cm. The distal end of the warming tube opens into and is enclosed by a distensible balloon made of latex rubber (wall thickness 0.005") which acts to direct the warm fluid flow from the inflow tube to the outflow tube. A stainless steel guide wire 11 cm in length with a shapeable tip, gently curved for the last 4 mm, is inserted into the guidewire lumen and is used to direct the distal end of the warming tube into the sphenoid sinus. The latex rubber balloon at the distal end of the warming tube expands into the sphenoid sinus once the outflow pressure head becomes positive following partial occlusion of the outflow. The circulation of cold saline inside the balloon cools the sphenoid sinus, the skull and the brain structures adjacent the sphenoid sinus, including the hypothalamus, and the animal begins to shiver. This physiological warming response is effective to raise the animal's body temperature.

EXAMPLE 15

This example illustrates the use of direct cooling in the hypothalamus to produce a physiological warming response. Standard imaging techniques are used to image the brain of the human patient prior to any surgical procedures. Accepted neurosurgical procedures are followed when exposing the skull and drilling a small hole in the skull 15, inserting a guide-tube under stereotactic control. After local anesthetic is applied, a Leksell stereotactic frame is applied to the head of a human patient and an incision in the scalp is made, exposing the skull. A single 3-mm twist drill hole is made in the exposed skull anterior to the coronal suture approximately 2 cm from the midline. The dura is penetrated with a sharp probe and a 1.1 mm guide tube is stereotactically placed in the cerebrum so that the tip is within 1 cm of the anterior hypothalamus. A sterile probe, with a working end and a distal end, is attached to a hydraulic microdrive. The distal end of the sterile probe is in thermal contact with the cold surface of an OptoTEC™ OT 0.8-18-FO Peltier cooler (manufactured by Melcor, 1040 Spruce Street, Trenton N.J. 08648). A portion of the sterile probe including the working end is positioned inside the guide tube. The sterile probe is advanced down the guide tube until a portion of the probe including the working end protrudes from the guide tube into the pre-optic/anterior hypothalamic region of the hypothalamus. Measurement of the temperature of the probe tip is used to control the power applied to the Peltier cooler such that the temperature drop at the electrode tip is limited to 1° C. The patient begins shivering within 5 minutes, and the patient's body temperature begins to rise.

EXAMPLE 16

This example illustrates the use of a chemical cooling device to produce a physiological warming response in a human patient. This chemical cooling device comprises a guide wire, fluid reservoirs and pumps, and a flexible polyethylene tube of outer diameter 0.1" with three lumens: two of 0.03" inner diameter, one of 0.015" inner diameter 16. The distal end of this tube is occluded with all three lumens opening into a common mixing chamber 17 of 0.08" diameter and 0.04" breadth. The chemical cooling device effects cooling near to its tip region by providing an endothermic reaction in the mixing chamber at its tip. In this example, the endothermic reaction is provided by dilution of a concentrated solution of ammonium nitrate. Distilled water flows in one of the larger diameter lumens, the lumen serving for inflow of distilled water; the other larger diameter lumen carries the outflow. The third, smallest lumen carries an aqueous mixture of 1 M ammonium nitrate. Liquid in all three tubes is maintained at a pressure less than ambient pressure to insure that, in the event of failure, no liquid will escape into the patient. Liquid flow is maintained by a siphon effect, with the two inflow reservoirs and one outflow reservoir being situated below the level of the patient's head. Ammonium nitrate solution is introduced into the mixing chamber by increasing the flow rate of that liquid (with a concomitant increase in outflow rate). This causes the ammonium nitrate solution to mix with and to be diluted in the distilled water, thereby absorbing heat in the region where mixing occurs. The chemical cooling device is used in the following manner: the distal end of the chemical cooling device is directed near to the sphenoid sinus as distilled water is flowing through the tube; when the tube is positioned as desired, ammonium nitrate solution flow is initiated, with an increase in the fluid outflow rate as well to insure adequate and appropriate removal of fluid from the mixing chamber situated in the distal end of the tube, thereby cooling the tip region of the chemical cooling device, cooling a sinus, and inducing a physiological warming response.

EXAMPLE 17

This example illustrates the induction of hyperthermia by cooling the hypothalamus as therapy for cancer. Hyperthermia may be induced by any method, such as the methods of Examples 13 through 16, in a patient suffering from cancer. In this example, hyperthermia is induced by the method of Example 15. Cooling is chronically maintained in the hypothalamus for as long as the probe is in place within the skull of the patient. Induction of hyperthermia is effective to slow the progression of the disease in the patient.

EXAMPLE 18

This example illustrates the induction of hyperthermia by cooling the 16 hypothalamus as an adjunct to cancer radiation therapy. Hyperthermia may be induced by any method, such as the methods of Examples 13 through 16, in a patient suffering from cancer that is susceptible to radiation treatment. In this example, hyperthermia is induced by the method of Example 15. Cooling of the hypothalamus, effective to induce hyperthermia, is maintained for a period of five hours, beginning prior to the initiation of each radiation therapy session. Induction of hyperthermia is effective to enhance the effectiveness of the radiation therapy, thereby aiding the treatment of the disease in the patient.

EXAMPLE 19

This example illustrates the induction of hyperthermia by cooling the hypothalamus as an adjunct to cancer chemotherapy. Hyperthermia may be induced by any method, such as any of the methods of Examples 13 through 16, in a patient suffering from cancer that is susceptible to chemotherapy treatment. The method of Example 15 is used to cool the hypothalamus of a patient undergoing chemotherapy for cancer, effective to induce hyperthermia in the patient during the time the patient receives his chemotherapy treatment. Five hours after the chemotherapy treatment session is completed, the hypothalamic cooling is curtailed, and the patient's body temperature returns to normal. The chemotherapy is much more effective than such treatment in the absence of the hyperthermia.

EXAMPLE 20

This example illustrates the induction of hyperthermia by cooling the hypothalamus as an adjunct to antiviral therapy. Hyperthermia may be induced by any method, such as any of the methods of Examples 13 through 16, in a patient suffering from a viral infection that is susceptible to antiviral therapy treatment. The method of Example 15 is used to cool the hypothalamus of a patient suffering from HIV infection and receiving drug therapy treatment for HIV infection, effective to induce hyperthermia (42° C.) in the patient for one hour. After the hypothalamic cooling is curtailed, the patient's body temperature returns to normal. Four days later, the hypothermia treatment is repeated. The drug therapy is much more effective than such treatment in the absence of the hyperthermia.

EXAMPLE 21

This example illustrates the placement of a chronic implant to provide local cooling near to the hypothalamus to produce a physiological warming response. Standard imaging techniques are used to image the brain of the human patient prior to any surgical procedures. Accepted neurosurgical procedures are followed when exposing the skull and drilling a small hole in the skull 15, inserting a guide-tube under stereotactic control. After local anesthetic is applied, a Leksell stereotactic frame is applied to the head of a human patient and an incision in the scalp is made, exposing a region of the left side of the skull. A single 3-mm twist drill hole is made in the exposed skull at a position superior to the temple approximately 2 cm inferior to the crown of the skull and approximately 1 cm posterior to the orbit. Care is taken that the dura mater 18 is not penetrated or damaged during the procedure. A sterile Peltier cooling device as described in Example 15 with attached wire leads threaded inside a flexible tube 20 is advanced into the hole 15 between the inside of the skull 19 and the dura mater 18 (flexible tube 20 is shown as a dotted line where it would be seen as behind the dura mater 18 in the view shown in FIG. 7). The wire leads are attached to a voltage source and voltage regulator. The Peltier device is advanced to a position near the hypothalamus outside the dura mater 18. A schematic illustration of the placement of such a device is shown in FIG. 7. The hole in the skull is filled with surgical cement. Voltage is applied to the thermocouple via the leads, effective to cool the Peltier device and to cool the hypothalamus of the patient. The patient's body temperature begins to rise. Patient response and temperature are monitored. If necessary or desired, voltage adjustments are made to provide the desired hypothalamic cooling. The incision is closed, with the leads and voltage source lying between the skull and skin of the patient. The implant is left in place for an extended period of several weeks to several months effective to provide chronic hypothalamic cooling for long-term hyperthermia.

Methods for Inducing Hypothermia for Cancer Treatment Using Heat Exchange Catheters A body lumen, such as an artery or vein, and fluids located therein, may be cooled by an apparatus which is cooler than the surrounding fluid and tissues. One such apparatus comprises a closed-ended flexible tube containing cool liquids, such as saline, with a large heat capacity effective to accept heat from surrounding fluid and tissue without significant rise in temperature of the cool liquids. A preferred means for preventing a rise in temperature of such cooled liquids is to provide for flow of such liquids out of the region desired to be cooled, and preferably out of the animal altogether, so that heat is effectively transferred out from the body of the animal. Alternatively, the heat exchange catheter may comprise a refrigerant, able to accept heat as it expands or changes state at a desired location within the catheter and, when the catheter is located within an animal, at a desired site within an animal's body. Such devices and methods are disclosed in, e.g., Ginsburg, U.S. Pat. No. 5,837,003; Ginsburg, U.S. Pat. No. 5,486,208; Ginsburg, U.S. Pat. No. 6,033,383; Philips et al., U.S. Pat. No. 6,019,783; and Dobak, U.S. Pat. No. 6,0510,19. The temperature of cool fluids enclosed or flowing within such a heat exchange catheter may be any temperature above freezing (e.g., above 0° C.), preferably between about 0° F. and 36° C., more preferably between about 20° C. and about 30° C.

Insertion of a heat exchange catheter into a patient and its positioning at a desired location within a body lumen of a patient may be accomplished by procedures for catheter placement well known in the art, following procedures in common use for cardiac catheterization for angiography, angioplasty, and other medical and diagnostic procedures. In order to cool an animal for cancer treatment, a heat exchange catheter may be placed into any suitable body lumen. Suitable body lumens include blood vessels, ventricles of the nervous system, lumens surrounding the spinal cord, and gastrointestinal tract lumens. In some embodiments of the methods of the invention, more than one body lumen may be provided with a heat exchange catheter during a treatment.

Local warming of cancerous tissue, during hypothermia, may be accomplished by application of a heated probe, or application of heated fluids, hot gas (such as warm or hot air, or other gases), heating pads, electric heaters, tubes or containers containing heated fluids, or the like. Alternatively, thermal radiation, whether infrared, microwave, or other radiation, may be directed to the cancerous tissue to maintain its temperature near to, or above, normal body temperature while the rest of the body is hypothermic. Similarly, ultrasound radiation may be applied to maintain the temperature of the cancerous tissue near to, or above, normal body temperature while the rest of the body is hypothermic. That is, during hypothermia, when substantially all of the rest of the animal experiences reduced body temperature, the temperature of the cancerous tissue is maintained at a temperature of between about 35° C. and about 44° C., preferably between about 35° C. to about 40° C., and most preferably between about 36° C. to about 38° C. In alternative embodiments, it is preferable to heat the cancerous tissue above body temperature while the rest of the animal is hypothermic and while a cancer treatment is applied. In this embodiment of the invention, the temperature of the cancerous tissue is maintained at a temperature of between about 38° C. and about 44° C.

When the treatment includes chemotherapy, standard chemotherapy regimens known in the art are applied. Chemotherapy regimens may use standard or nonstandard chemotherapy drugs including as methotrexate, 5-fluoruracil, doxorubicin, cisplatin, taxol, and other drugs, individually or in combination. The dosage of drug or drugs used can depend upon various factors, such as the mode of administration, species, age, weight and individual state. The doses to be administered daily are about 0.05 to about 100 mg/kg body weight per individual component. The amount of the particular active material per form of administration can be from about 5 to about 1000 mg.

When the treatment includes radiation treatment, standard radiation therapy regimens known in the art are applied. Typical radiotherapy regimens include exposure of cancerous tissue to ionizing radiation daily (e.g., five times per week) for about 5 or more weeks, where both the length of treatment and the total dosage of radiation are dictated by the tumor size, location, tumor type, and other factors known in the art. For example, treatment regimens for small microscopic tumors typically include daily exposure of the tumor to ionizing radiation for approximately 5 weeks with a cumulative ionizing radiation dosage of about 4500–5000 rads. Treatment regimens for larger tumors as well as tumors located in the head and neck typically are extended to 8 or more weeks and can employ a cumulative ionizing radiation dosage of about 7400 or more rads.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE 22

This example illustrates the use of heat exchange catheter to induce hypothermia in a human subject suffering from cancer-related pain. A heat exchange catheter is introduced into the femoral artery of the subject via a groin puncture and located in the aorta at least a few centimeters from the aortic arch by standard clinical procedures used for, e.g., angioplasty. The surface of the heat exchange catheter is maintained at a temperature of 22° C. and the tympanic and rectal temperature of the subject is monitored. Within approximately 30 minutes, the subject's body temperature is below 32° C. The subject experiences relief of cancer-related pain.

EXAMPLE 23

This example illustrates the use of a heat exchange catheter to induce hypothermia in a patient suffering from cancer to enhance the efficacy of a cancer treatment. As described in Example 22, a heat exchange catheter is introduced into the femoral artery of the subject via a groin puncture and located in the aorta at least a few centimeters from the aortic arch by standard clinical procedures used for, e.g., angioplasty. The surface of the heat exchange catheter is maintained at a temperature of 22° C. and the tympanic and rectal temperature of the subject is monitored. Within approximately 30 minutes, the subject's body temperature is below 32° C. Hypothermia is maintained for a period of five hours, beginning prior to the initiation of a radiation therapy session. Radiation treatment is applied to cancerous tissue in the patient's body while the patient's body temperature is maintained below 32° C. Induction of hypothermia is effective to enhance the effectiveness of the radiation therapy, thereby aiding the treatment of the disease in the patient.

EXAMPLE 24

This example illustrates the use of a heat exchange catheter to induce hypothermia in a patient suffering from cancer to enhance the efficacy of a cancer treatment. Hypothermia is induced in the patient by the method of Example 22 and is maintained for a period of five hours, beginning prior to the initiation of a cancer chemotherapy session. Cancer chemotherapy treatment is applied to cancerous tissue in the patient's body while the patient's body temperature is maintained below 32° C. Induction of hypothermia is effective to enhance the effectiveness of the cancer chemotherapy treatment, thereby aiding the treatment of the disease in the patient.

EXAMPLE 25

This example illustrates the use of a heat exchange catheter to induce hypothermia in a patient suffering from cancerous tissue located near to the subject's skin to enhance the efficacy of a cancer treatment in conjunction with warming of the patient's cancerous tissue. Hypothermia is induced in the patient by the method of Example 22 and is maintained for a period of five hours, beginning prior to the initiation of a radiation therapy session. Radiation therapy treatment is applied to cancerous tissue in the patient's body while the patient's body temperature is maintained below 32° C. The cancerous tissue in the patient is maintained at normal body temperature by the application of a warming pad slightly larger in area than the area of cancerous tissue to the skin near to the cancerous tissue. The pad is heated by circulating warm water within the pad. Induction of hypothermia while maintaining the cancerous tissue at a temperature between 36° C. and 38° C., is effective to enhance the effectiveness of the radiation therapy, thereby aiding the treatment of the disease in the patient. Induction of hypothermia in conjunction with maintenance of cancerous tissue at a temperature near to normal body temperature is effective to enhance the effectiveness of the cancer radiation therapy treatment, thereby aiding the treatment of the disease in the patient.

EXAMPLE 26

This example illustrates the induction of hypothermia with a heat exchange catheter as an adjunct to cancer radiation therapy. Hypothermia is induced by the method of Example 22 in a patient suffering from prostate cancer that is susceptible to radiation treatment. Hypothermia is maintained for a period of five hours, beginning prior to the initiation of each radiation therapy session. The cancerous prostate tissue in the patient is maintained at normal body temperature by the direction of ultrasound energy to the cancerous prostate. The prostate is warmed by an ultrasound probe inserted via the urethra, by the method of Andrus et al., U.S. Pat. No. 5,895,356. Induction of hypothermia while maintaining the cancerous prostate at a temperature between 36° C. and 38° C. is effective to enhance the effectiveness of the radiation therapy, thereby aiding the treatment of the disease in the patient.

EXAMPLE 27

This example illustrates the induction of hypothermia with a heat exchange catheter as an adjunct to cancer chemotherapy. Hypothermia is induced by the method of Example 22 in a patient suffering from prostate cancer that is susceptible to chemotherapy treatment. The subject's prostate is warmed by an ultrasound probe inserted via the urethra, by the method of Andrus et al., U.S. Pat. No. 5,895,356. The prostate itself is maintained at a temperature between 36° C. and 38° C. while the temperature of the rest of the patient is reduced to below 32° C. Five hours after the chemotherapy treatment is completed, the heat exchange catheter is withdrawn from the patient and the patient's body temperature returns to normal. The chemotherapy is more effective than such chemotherapy treatment would be in the absence of the temperature differential between the cancerous tissue and the rest of the body.

EXAMPLE 28

This example illustrates the induction of hypothermia with a heat exchange catheter as an adjunct to combined cancer radiation therapy and cancer chemotherapy. Hypothermia is induced by the method of Example 22 in a patient suffering from prostate cancer that is susceptible to chemotherapy and to radiation treatment. Hypothermia is maintained for a period of five hours, beginning prior to the initiation of each radiation and chemotherapy session. The cancerous prostate tissue in the patient is maintained at normal body temperature by the direction of ultrasound energy to the cancerous prostate. The prostate is warmed by an ultrasound probe inserted via the urethra, by the method of Andrus et al., U.S. Pat. No. 5,895,356. Induction of hypothermia while maintaining the cancerous prostate at a temperature between 36° C. and 38° C. is effective to enhance the effectiveness of the combined radiation and chemotherapy, thereby aiding the treatment of the disease in the patient.

It is to be understood that while the invention has been described in conjunction with preferred specific embodiments thereof, the foregoing description, including the specific examples disclosed, are intended to illustrate and not limit the scope of the invention. Other aspects, advantages and modifications within the scope of the invention will be apparent to those skilled in the art to which the invention pertains.

I claim:

1. A method for treating a neurological disorder in an animal with a hypothalamus, comprising:
   providing a warming means;
   directing heat from said warming means to said hypothalamus to cause the animal to respond to said heat with a physiological cooling response to induce hypothermia in said animal effective to treat said neurological disorder; further comprising:
   applying a cooling means to said animal while applying said warming means.

2. The method of claim 1, wherein said neurological disorder comprises neurological damage.

3. The method of claim 1, wherein said neurological disorder comprises neurological damage resulting from the group of disorders and traumas consisting of cardiac arrest, stroke, trauma, and other such conditions.

4. The method of claim 1, wherein said neurological disorder comprises stroke.

5. The method of claim 3, wherein said trauma comprises head trauma.

6. The method of claim 1 for treating a neurological disorder in an animal with a hypothalamus, said animal further possessing an oral passage and a nasal passage and a sinus passage, further comprising the step of applying said warming means via a nasal or oral passage to a sinus passage, effective to cause said animal to respond to said heat with a physiological cooling response effective to induce hypothermia in said animal effective to treat said neurological disorder.

7. The method of claim 1 wherein said step of applying said warming means comprises applying heat within said hypothalamus.

8. The method of claim 1 wherein said cooling means is chosen from the group of cold coverings, moving air, cold fluids, intravenously injected cold fluids, muscle relaxants, drug treatments, breathing cold gases, wetting skin, wetting hair, cold support and peritoneal lavage.

9. The method of claim 1 wherein said warming means comprises an electrical device comprising a small region capable of generating heat in response to current flow or voltage, effective to warm said hypothalamus.

10. The method of claim 1, wherein said warming means comprises a chemical warming device.

11. The method of claim 1, wherein said warming means comprises electromagnetic radiation.

12. The method of claim 1 wherein said warming means is effective to warm said hypothalamus to between about 37.2° C. and about 43° C.

13. The method of claim 1, further comprising the step of providing a directing means effective to direct heat from said warming means to said hypothalamus.

14. The method of claim 13, wherein said directing means are effective to direct heat within said hypothalamus.

15. The method of claim 1, wherein said warming means is effective to warm said sinus to between about 38° C. and about 50° C. and is effective to warm said hypothalamus to between about 37.2° C. and about 43° C.

16. The method of claim 1, wherein said warming means comprises a distal portion, further comprising the step of placing at least said distal portion of said warming means within said animal.

17. The method of claim 11, wherein said warming means comprises a distal portion, further comprising the step of placing at least said distal portion of said warming means within said animal.

* * * * *